United States Patent [19]

Konz et al.

[11] 4,309,566

[45] Jan. 5, 1982

[54] PLANT REGULATOR

[75] Inventors: Marvin J. Konz, Lockport; Norman E. Krog, Middleport, both of N.Y.

[73] Assignee: FMC Corporation, Philadelphia, Pa.

[21] Appl. No.: 91,604

[22] Filed: Nov. 5, 1979

[51] Int. Cl.³ .............................................. C07C 69/76
[52] U.S. Cl. ........................................ 560/110; 71/76; 71/86; 71/105; 71/107; 260/465 D; 260/952; 560/62; 560/65; 560/72; 560/73; 560/74; 560/103; 560/106
[58] Field of Search ...................... 560/110, 103, 106; 71/107

[56] References Cited

U.S. PATENT DOCUMENTS

| | | | |
|---|---|---|---|
| 2,260,628 | 10/1941 | Kyrides | 560/103 |
| 2,606,205 | 8/1952 | Shelton et al. | 560/110 |
| 2,992,913 | 7/1961 | Pfeiffer | 71/107 |
| 3,467,697 | 9/1969 | Kohll et al. | 560/106 |
| 3,518,074 | 6/1970 | Veno et al. | 560/110 |
| 3,941,580 | 3/1976 | Hokama | 71/107 |
| 3,944,411 | 3/1976 | Rohr | 71/107 |
| 4,084,062 | 4/1978 | Mihailovski | 560/106 |

OTHER PUBLICATIONS

Boudreau et al., "Hydrolyses of O-acyl, etc.", (1976), J. Chem. Soc. Perkin II, pp. 1221–1225, (1977).

*Primary Examiner*—Glennon H. Hollrah
*Attorney, Agent, or Firm*—Harrison H. Young, Jr.; H. Robinson Ertelt; Robert L. Andersen

[57] ABSTRACT

Novel substituted benzoyloxy compounds exhibit plant regulator activity, retarding or stimulating the growth of a variety of broadleaved plants, while leaving grasses unaffected. The preparation and plant regulator activity of the compounds is exemplified.

4 Claims, No Drawings

PLANT REGULATOR

This invention pertains to the general field of plant regulators and particularly to compositions which control and regulate plant growth by retarding or stimulating growth. Plant regulators are defined in the U.S. Department of Agriculture publication Interpretation Number 3 of the Regulations for the Enforcement of the Federal Insecticide, Fungicide, and Rodenticide Act (Revision 1, November 1964) at Section 362-101 (a)(11).

Novel plant regulators are described which retard or stimulate the growth of many broadleaved plants while leaving grasses unaffected. No reference has been found which discloses the plant regulator activity of compositions of the present invention, or the active ingredients thereof.

The plant regulator compositions of this invention contain as active ingredient a compound of the formula

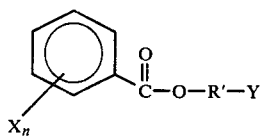

wherein R′ is straight or branched alkylene of 1 to 4 carbons or phenylene; Y is

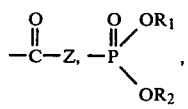

—CN, or —H,
with the proviso that when
R′ is phenylene, Y is —CN or —H;
Z is —NH$_2$, —NHR$_1$, —NR$_1$R$_2$, —NH—NR$_1$R$_2$, —OH, —O$^\ominus$ M$^\oplus$, —OR$_1$;
R$_1$ and R$_2$ are the same or different and are alkyl or 1 to 4 carbon atoms, optionally substituted with halogen, or phenyl, optionally substituted with halogen, alkyl, or alkoxy;
M$^\oplus$ is sodium or potassium;
X is halogen, methyl, or methoxy, which may be the same or different when n is greater than 1;
n is 0 to 3.

Preferred compounds are those in which R′ is alkylene of 1 to 3 carbon atoms; R$_1$ and R$_2$ are methyl or ethyl; X is chlorine; n is 1 to 3.

Particularly preferred compounds are those in which R′ is methylene; Y is

and Z is —NH$_2$, —NR$_1$R$_2$, or —OR$_1$.

More particularly preferred compounds are those in which X$_n$ consists of 2,6-dichloro.

In general the compounds of the invention were prepared by causing the sodium or potassium salt of a substituted benzoic acid, for example, 2,6-dichlorobenzoic acid, to react in the presence of 1,4,7,10,13,16-hexaoxacyclooctadecane ("18-crown-6") in a solvent with an entity Q—R′—Y in which Q is chlorine or bromine and —R′—Y is as defined above. Alternatively the substituted benzoic acid was converted to the corresponding benzoyl chloride with thionyl chloride, and the benzoyl chloride caused to react in a solvent with HO—R′—Y in the presence of an acid acceptor such as triethylamine or pyridine.

Preparation of the compounds of the invention, and of selected intermediates from which they are prepared, is exemplified below. In the description which follow, all temperatures are in degrees centigrade, and reduced pressures are in millimeters of mercury, or if not otherwise specified, were obtained by means of a water aspirator.

EXAMPLE I (Aminocarbonyl)Methyl 2,6-Dichlorobenzoate

A sample of 5.9 grams (0.105 mole) of potassium hydroxide was ground to a powder and placed in the reaction vessel. To this was added 270 ml of dry toluene, followed by 20.0 grams (0.105 mole) of 2,6-dichlorobenzoic acid. The stirred reaction mixture was heated under reflux while the water by-product was collected by azeotropic distillation using a Dean-Stark trap. A total of 2.8 ml of water was collected during a 30-minute period. At the end of this time the reaction mixture was cooled slightly and 2.0 grams of 1,4,7,10,13,16-hexaoxacyclooctadecane, followed by 9.8 grams (0.105 mole) of chloroacetamide were added. Upon completion of the addition the reaction mixture was heated under reflux for 18 hours. the reaction mixture was cooled to ambient temperature and the toluene layer was separated from the two-phase system and washed with one portion of 100 ml of water. An emulsion formed but was broken up by the addition of 100 ml of ethyl acetate. The organic layer was separated and dried with sodium sulfate. The mixture was filtered, and the filtrate evaporated under reduced pressure to a residual semi-solid. The solid was recrystallized twice from high-boiling petroleum ether-ethyl acetate using decolorizing carbon to give 12.6 grams of (aminocarbonyl)methyl 2,6-dichlorobenzoate; mp 113.5°–115.5°. The ir and the nmr spectra were consistent with the proposed structure.

Analyses calc'd for C$_9$H$_7$Cl$_2$NO$_3$: C 43.57; H, 2.84; N 5.65; Found: C 43.43; H 2.92; N 5.66.

EXAMPLE II (Aminocarbonyl)Methyl 2,6-Difluorobenzoate

This compound was prepared in the manner of Example I, using 10.0 grams (0.063 mole) of 2,6-difluorobenzoic acid, 4.2 grams (0.063 mole) of potassium hydroxide, 5.9 grams (0.063 mole) of 2-chloroacetamide, and 1.7 grams of 1,4,7,10,13,16-hexaoxacyclooctadecene in 250 ml of dry toluene. The crude product was recrystallized once with ethyl acetate, then with ethyl acetate-hexane, using decolorizing carbon. The yield was 5.2 grams of (aminocarbonyl)methyl 2,6-difluorobenzoate; mp 108.5°–110°. The ir and the nmr spectra were consistent with the proposed structure.

Analyses calc'd for C$_9$H$_7$F$_2$NO$_3$: C 50.24; H 3.28; N 6.51; Found: C 50.28; H 3.35; N 6.60.

EXAMPLE III (Aminocarbonyl)Methyl 2,6-Dimethylbenzoate

This compound was prepared in the manner of Example I, using 10.0 grams (0.067 mole) of 2,6-dimethylbenzoic acid. The crude product was recrystallized from hexaneethyl acetate to give 4.5 grams of (aminocarbonyl)methyl 2,6-dimethylbenzoate; mp 106.5°–107.5°. The ir and the nmr spectra were consistent with the proposed structure.

Analyses calc'd for $C_{11}H_{13}NO_3$: C 63.76; H 6.32; N 6.76; Found: C 63.54; H 6.22; N 6.87.

EXAMPLE IV (Aminocarbonyl)Methyl 2-Chlorobenzoate

This compound was prepared in the manner of Example I, using 10.0 grams (0.064 mole) of 2-chlorobenzoic acid. The crude product was recrystallized from toluene to give 4.9 grams of (aminocarbonyl)methyl 2-chlorobenzoate; mp 117°–120°. The ir and the nmr spectra were consistent with the proposed structure.

Analyses clc'd for $C_9H_8ClNO_3$: C 50.60; H 3.77; N 6.56; Found: C 50.51; H 3.79; N 6.50.

EXAMPLE V (Aminocarbonyl)Methyl 2,3,6-Trichlorobenzoate

This compound was prepared in the manner of Example I, using 15.0 grams (0.066 mole) of 2,3,6-trichlorobenzoic acid, 4.4 grams (0.066 mole) of potassium hydroxide, 6.2 grams (0.066 mole) of 2-chloroacetamide, and 1.8 grams of 1,4,7,10,13,16-hexaoxacyclooctadecane in 300 ml of dry toluene and 200 ml of dimethylformamide. The crude product was purified by liquid chromatography, followed by recrystallization from ethyl acetate. The yield was 0.9 gram of (aminocarbonyl)methyl 2,3,6-trichlorobenzoate; mp 158°–160°. The ir and the nmr spectra were consistent with the proposed structure.

Analyses calc'd for $C_9H_6Cl_3NO_3$: C 38.26; H 2.14; N 4.96; Found: C 38.40; H 2.20; N 5.06.

EXAMPLE VI (Aminocarbonyl)Methyl Benzoate

In the reaction vessel, 4.3 grams (0.09 mole) of a 50% suspension of sodium hydride in mineral oil was washed with two portions of 50 ml each of hexane, then two portions of 50 ml each of toluene. Dry toluene, 75 ml, was added and with stirring a solution of 10.0 grams (0.082 mole) of benzoic acid in 200 ml of dry toluene was added dropwise. The exothermic reaction caused the temperature of the reaction mixture to rise from 27° to 32°. Upon completion of the addition, the reaction mixture was heated under reflux for 1.5 hour. The mixture was cooled to ambient temperature and 8.4 grams (0.09 mole) of 2-chloroacetamide was added in portions. Upon completion of the addition, the reaction mixture was heated under reflux for 18 hours. An additional 150 ml of dry toluene was added and heating under reflux continued an additional 24 hours. The reaction mixture was cooled to ambient temperature and a solid precipitate collected by filtration. The filtrate was extracted with two portions of 200 ml each of water. The milky organic layer was dried twice with sodium sulfate and filtered. the filtrate was evaporated under reduced pressure to a solid residue, which produced bubbling in the presence of aqueous saturated sodium bicarbonate solution, and was concluded to be unreacted benzoic acid. The solid collected by filtration from the original reaction mixture was dissolved in 200 ml of ethyl acetate and washed with two portions of 100 ml each of water. The organic layer was dried with sodium sulfate and filtered. The filtrate was evaporated under reduced pressure to a solid residue. The solid was recrystallized from toluene to give 3.7 grams of (aminocarbonyl)methyl benzoate; mp 118°–120 . The ir and the nmr spectra were consistent with the proposed structure.

Analyses calc'd for $C_9H_9NO_3$: C 60.32; H 5.06; N 7.82; Found: C 60.23; H 5.02; N 7.88.

EXAMPLE VII (Diethylaminocarbonyl)Methyl 2,6-Dichlorobenzoate

This compound was prepared in the manner of Example I. The crude product was recrystallized from 4:1 hexane: ethyl acetate to give 7.0 grams of (diethylaminocarbonyl)methyl 2,6-dichlorobenzoate; mp 62.5–63.5. The ir and the nmr spectra were consistent with the proposed structure.

Analyses calc'd for $C_{13}H_{19}Cl_2NO_3$: C 51.33; H 4.97; N 4.61; Found: C 51.50; H 5.06; N 4.71.

EXAMPLE VIII 2,6-Dichlorobenzoyloxyacetic Acid 2,2-Dimethylhydrazide

Step A: Synthesis of chloroacetic acid 2,2-dimethylhydrazide

To a stirred solution of 33.9 grams (0.30 mole) of chloroacetyl chloride in 300 ml of chloroform, under an argon atmosphere and at 0°–2°, was added dropwise a solution of 18.0 grams (0.30 mole) of 1,1-dimethylhydrazine in 150 ml of chloroform. The addition required 1 hour and when it was completed the reaction mixture was allowed to warm to ambient temperature where it was stirred for 16 hours. The reaction mixture was evaporated under reduced pressure to a solid residue. The solid was dissolved in 70 ml of water and brought to pH 8 with solid sodium carbonate. The mixture was extracted with four portions of 50 ml each of chloroform. The combined extracts were washed with one portion of 50 ml of an aqueous solution saturated with sodium chloride. The organic layer was dried with sodium sulfate and filtered. The filtrate was evaporated under reduced pressure to a waxy solid residue. Higher boiling volatiles were removed by evacuation using a vacuum pump. The residue was recrystallized from methylcyclohexane to give a white solid; mp 74.5°–130°. The solid was slurried in 150 ml of ethyl acetate and filtered to remove a polymer-like material. The filtrate was evaporated under reduced pressure to give 10.8 grams of solid chloroacetic acid 2,2-dimethylhdrazide, mp 74.5°–76°. The ir and nmr spectra were consistent with the proposed structure.

Analyses calc'd for $C_4H_9ClN_2O$: C 35.18; H 6.64; N 20.51; Found: C 34.89; H 6.38; N 20.39.

Step B: Synthesis of 2,6-dichlorobenzoyloxyacetic acid 2,2-dimethylhydrazide

This compound was prepared in the manner of Example I, using 12.2 grams (0.064 mole) of 2,6-dichlorobenzoic acid, 4.2 grams (0.064 mole) of potassium hydroxide, 8.7 grams (0.064 mole) of chloroacetic acid 2,2-dimethylhydrazide, and 1.7 grams of 1,4,7,10,13,16-hexaoxacyclooctadecane in 180 ml of dry toluene. The crude product was recrystallized twice from ethyl acetate using decolorizing carbon to give 18.6 grams of 2,6-dichlorobenzoyloxyacetic acid 2,2-dimethylhydrazide; mp 160°–162°. The ir and the nmr spectra were consistent with the proposed structure.

Analyses calc'd for $C_{11}H_{12}Cl_2N_2O_3$: C 44.84; H 3.95; N 9.66; Found: C 44.75; H 4.11; N 9.50.

EXAMPLE IX

(Ethoxycarbonyl)Methyl 2,6-Dichlorobenzoate

This compound was prepared in the manner of Example I, using 8.7 grams (0.052 mole) of ethyl bromoacetate. The crude product was recrystallized from hexane to give 6.5 grams of (ethoxycarbonyl)methyl 2,6-dichlorobenzoate; mp 50°–51°. The ir and the nmr spectra were consistent with the proposed structure.

Analyses calc'd for $C_{11}H_{10}Cl_2O_4$: C 47.68; H 3.64; Found: C 47.63; H 3.79.

EXAMPLE X

Carboxymethyl 2,6-Dichlorobenzoate

Potassium hydroxide, 0.8 gram (0.012 mole), was powdered and dissolved in 50 ml of ethanol. The solution was warmed to 40°–50° and 3.1 grams (0.011 mole) of (ethoxycarbonyl)methyl 2,6-dichlorobenzoate (the compound of Example IX) was added in portions during a 5-minute period. Upon completion of the addition a precipitate formed. The reaction mixture was stirred at ambient temperature for 18 hours. The potassium salt was collected by filtration, washed with ethanol, dried, placed in an Erlenmeyer flask, and stirred with 50 ml of water. To the resultant solution was added a solution of 10 ml of concentrated hydrochloric acid in 40 ml of water. The solid precipitate was collected by filtration and washed with water. The filter cake was dissolved in 100 ml of ethyl acetate and dried with sodium sulfate. The mixture was filtered and the filtrate evaporated under reduced pressure to give 1.1 grams of carboxymethyl 2,6-dichlorobenzoate; mp 180°–181.5°. The nmr and the ir spectra were consistent with the proposed structure.

Analyses calc'd for $C_9H_6Cl_2O_4$: C 43.40; H 2.43; Found: C 43.48; H 2.70.

EXAMPLE XI

Sodium 2,6-Dichlorobenzoyloxyacetate

To a stirred solution of 6.0 grams (0.024 mole) of carboxymethyl 2,6-dichlorobenzoate (the compound of Example X) in 100 ml of ethanol was added a solution of 0.9 gram (0.022 mole) of sodium hydroxide in 50 ml of ethanol. The reaction mixture was stirred for 1.75 hours during which time a solid precipitate formed. The solid was collected by filtration and washed with ethanol. The filtrate was concentrated to a volume of 50 ml, and a second crop of solid was collected by filtration. The solids were combined to give 3.7 grams of sodium 2,6-dichlorobenzoylacetate; mp 241° (decomposes). The nmr and the ir spectra were consistent with the proposed structure.

Analyses calc'd for $C_9H_5Cl_2O_4Na$: C 39.88; H 1.86; Found: C 39.81; H 2.03.

EXAMPLE XII

Cyanomethyl 2,6-Dichlorobenzoate

This compound was prepared in the manner of Example 1, using 10.0 grams (0.052 mole) of 2,6-dichlorobenzoic acid, 2.9 grams (0.052 mole) of potassium hydroxide, 3.9 grams (0.052 mole) of chloroacetonitrile, and 1.4 grams of 1,4,7,10,13,16-hexaoxacyclooctadecane in 160 ml of dry toluene. The crude product was distilled to give 7.3 grams of cyanomethyl 2,6-dichlorobenzoate; bp 107°/0.006 mm. The ir and the nmr spectra were consistent with the proposed structure.

Analysis calc'd for $C_9H_5Cl_2NO_2$: C 46.99; H 2.10; N 6.09; Found: C 46.66; H 2.30; N 5.91.

EXAMPLE XIII

1-Cyanoethyl 2,6-Dichlorobenzoate

A solution of 2.4 grams (0.033 mole) of 1-hydroxypropionitrile in 150 ml of diethyl ether was prepared, and with stirring 3.7 grams (0.036 mole) of triethylamine was added in one portion. A second solution of 7.0 grams (0.033 mole) of 2,6-dichlorobenzoyl chloride in 50 ml of diethyl ether was prepared and was added dropwise to the stirred first solution during a 12 minute period, the temperature remaining at 27°. Upon complete addition the reaction mixture was stirred at ambient temperature for approximately 110 hours. The reaction mixture was filtered to remove triethylamine hydrochloride. The filtrate was concentrated under reduced pressure to a semi-solid. The semi-solid was slurried in hexane and ethyl acetate was added until a white crystalline solid formed. The solid was collected by filtration and washed with ethyl acetate. The filtrate and wash were combined and concentrated under reduced pressure to a yellow oil. The oil was distilled in three fractions; bp range 42°–65°/0.44 mm. The pot residue from the distillation solidified and was recrystallized from ethanol using charcoal as a decolorizing agent. The recrystallization gave a white crystalline solid, mp 73°–75°. Nuclear magnetic resonance spectroscopy indicated the solid to be impure product. A second crop of solid was obtained from the recrystallization by adding water to the filtered mother liquor. The two crops of solid were combined and recrystallized from methylcyclohexane, then from hexane. The yield of pure 1-cyanoethyl 2,6-dichlorobenzoate was 1.1 grams; mp 76°–77°. The nmr spectra was consistent with the proposed structure.

Analysis calc'd for $C_{10}H_7Cl_2NO_2$: C 49.21; H 2.89; N 5.74; Found: C 49.04; H 2.93; N 5.47.

EXAMPLE XIV

2-Cyanoethyl 2,6-Dichlorobenzoate

A solution of 3.7 grams (0.052 mole) of 2-hydroxypropionitrile in 8.9 grams (0.10 mole) of pyridine was prepared. To this stirred solution at ambient temperature was added 10.4 grams (0.05 mole) of 2,6-dichlorobenzoyl chloride dropwise during a 20 minute period. The exothermic reaction caused the temperature of the reaction mixture to rise to 50°. The reaction mixture was heated at 75°–80° for 75 minutes. The cooled reaction mixture was poured into 150 ml of water and the mixture was stirred. The mixture was extracted with 200 ml of diethyl ether. The extract was washed with three portions of 30 ml each of an aqueous solution of 3% hydrochloric acid, then three portions of 30 ml each of water. The organic layer was dried with sodium sulfate and filtered. The filtrate was concentrated under reduced pressure to an amber oil. The oil solidified and the solid was recrystallized from hexane-diethyl ether to give an oily semi-solid. The semi-solid and mother liquor were combined and concentrated under reduced pressure to an oil. An attempt to sublime the oil failed. The oil was distilled under reduced pressure using a short-path distilling system to give 3.1 grams of 2-cyanoethyl 2,6-dichlorobenzoate; bp 117°/0.005 mm. The oil product solidified; mp 45°–46° C. The nmr and the ir spectra were consistent with the proposed structure.

EXAMPLE XV

Diethyl (2,6-Dichlorobenzoyloxy)methylphosphonate

To a stirred solution of 5.8 grams (0.25 mole) of sodium metal in 150 ml of diethyl ether, under an argon atmosphere and at 15°–20°, was added dropwise 34.5 grams (0.25 mole) of diethyl phosphite. Complete addition required 60 minutes. Upon completion of the addition, the reaction mixture was kept at 15°–20° for 1 hour, then heated under reflux for 1 hour. The reaction mixture was cooled to 15° and 9.0 grams (0.30 mole) of paraformaldehyde was added in portions during a 10–15 minute period. Upon completion of the addition the reaction mixture was stirred at ambient temperature for 18 hours. After this period 52.4 grams (0.25 mole) of 2,6-dichlorobenzoyl chloride in 50 ml of diethyl ether was added dropwise during a 37-minute period. Upon completion of the addition the reaction mixture was stirred for 1.5 hours, then filtered. The filtrate was evaporated under reduced pressure to a residual oil. Impurities were removed from the residual oil by high vacuum distillation. The pot residue was subjected to column chromatography on 600 grams of silica gel using ethyl acetate as eluent. The appropriate fractions were combined and distilled under high vacuum to give 13.6 grams of diethyl (2,6-dichlorobenzoyloxy)methylphosphonate; bp 164°–167°/0.01 mm. The nmr and the ir spectra were consistent with the proposed structure.

Analyses calc'd for $C_{12}H_{15}Cl_2O_5O$: C 42.25; H 4.43; P 9.08; Found: C 42.03; H 4.34; P 8.82.

The procedures exemplified previously were used to prepare the following compounds of the invention:

| Example | |
|---|---|
| XVI | Diethyl 2-[(2,6-dichlorobenzoyl)oxy]propylphosphonate; mp 62–66°; C 45.25%, H 4.99%, P 8.26%. |
| XVII | 3-(Ethoxycarbonyl)propyl 2,6-dichlorobenzoate; bp 133–136°/0.009 mm; C 50.89%, H 4.35%. |
| XVIII | 3-Carboxypropyl 2,6-dichlorobenzoate; bp 160–164°/0.003–.005 mm. |
| XIX | Methyl 2,6-dichlorobenzoate; bp 56°/0.007 mm; C 46.60%, H 2.82%. |
| XX | Ethyl 2,6-dichlorobenzoate; bp 76°/0.012 mm; C 49.09%, H 3.67%. |
| XXI | Butyl 2,6-dichlorobenzoate; bp 89°/0.008 mm; C 53.47%, H 4.92%. |
| XXII | 4-Cyanophenyl 2,6-dichlorobenzoate; mp 144–142.5°; C 57.75%, H 2.67%, N 4.72%. |
| XXIII | (Methoxycarbonyl)methyl 2,6-dichlorobenzoate; mp 80.5–82°; C 45.84%, H 3.17%. |
| XXIV | (Butoxycarbonyl)methyl 2,6-dichlorobenzoate; bp 152–155°/0.014 mm; C 50.99%, H 4.43%. |
| XXV | (1,1-Dimethylethoxycarbonyl)methyl 2,6-dichlorobenzoate; mp 77–78.5°; C 51.05%, H 4.59%. |
| XXVI | (Phenoxycarbonyl)methyl 2,6-dichlorobenzoate; mp 87–87.5°; C 55.29%; H 3.39%. |
| XXVII | (Dimethylaminocarbonyl)methyl 2,6-dichlorobenzoate; mp 74.5–75.5°; C 47.82%, H 4.02%, N 4.91%. |
| XXVIII | (Ethylaminocarbonyl)methyl 2,6-dichlorobenzoate; mp 88–89°; C 47.70%, H 3.85%; N 4.96%. |
| XXIX | (Butylaminocarbonyl)methyl 2,6-dichlorobenzoate; mp 55.5–56.5°; C 51.54%, H 5.01%, N 4.78%. |
| XXX | (Phenylaminocarbonyl)methyl 2,6-dichlorobenzoate; mp 114–115°; C 55.82%; H 3.44%, |

| Example | |
|---|---|
| | N 4.17%. |

EXAMPLE XXXI

Initial Biological Screening Tests

The test species used in the initial screening tests for plant regulator activity were lima bean (*Phaseolus limensis* Macfad.), sweet corn (*Zea mays* L.), wild oats (*Avena fatua* L.), lettuce (*Lactuca sativa* L.), mustard (*Brassica juncea* (L.) Cosson) and crabgrass (*Digitcria sanguinalis* (L.) Scop.).

For the preemergence test, seeds of the test species were planted in 15×20×8 cm flats containing approximately a 5 cm depth of sandy loam soil. Prior to seeding, the rows were marked by pressing a wooden template onto the soil surface. A fungicidal treatment was sprinkled onto the seeds after sowing. The flats are then watered lightly to break the surface tension. An aqueous acetone spray solution containing the compound of Example I was then applied directly to the soil and exposed seeds at rates equivalent to 8.96 kg active ingredient per hectare. A thin layer of soil (approximately 1.0 cm) was then applied to the surface of the flat. The test plants were maintained in a greenhouse and watered regularly on the soil surface for a period of 10 to 14 days. At this time stunting of lima beans by the compound of Example I was observed. This is a plant regulatory response. There was no effect on the other plant species.

For the postemergence test, seeds of the test species were planted in 15×20×8 cm flats containing approximately a 5 cm depth of sandy loam soil. Prior to seeding the rows were marked by pressing a wooden template onto the soil surface. A fungicidal treatment was sprinkled onto the seeds after sowing. A thin layer of soil (approximately 1.0 cm) was then applied to the surface of the flat. The flats were maintained in a greenhouse and watered regularly on the soil surface for a period of 10 to 14 days. At this time the first trifoliate leaves of the bean plants were unfolding. The test plants were then sprayed with the aqueous acetone spray solution containing the compound of Example I at rates equivalent to 8.96 kg active ingredient per hectare. The treated plants were maintained in the greenhouse and watered regularly for an additional 10 to 14 days at which time lima bean and corn exhibited necrosis and lettuce and mustard exhibited nastic response to the compound of Example I. These are plant regulatory responses.

EXAMPLE XXXII

Primary Evaluation Tests At Multiple Rates of Application

In primary evaluation tests of plant regulator activity, flats were seeded as for the initial screening tests. In addition to the six plant species utilized in the initial screening tests, additional species used to assess plant regulator activity of the compounds of the invention were:

| | |
|---|---|
| soybean | (*Glycine max* (L.) Merv.) |
| common ragweed | (*Ambrosia artemisiifolia* L.) |
| tall morningglory | (*Ipomoea purpurea* (L.) Roth) |
| Pennsylvania smartweed | (*Polygonum pensylvanicum* L.) |
| velvetleaf | (*Abutilon theophrasti* Medic.) |

| | -continued |
|---|---|
| jimsonweed | (*Datura stramonium* L.) |
| lambsquarter | (*Chenopodium album* L.) |
| barnyardgrass | (*Echinochloa crusgalli* (L.) Beauv.) |
| green foxtail | (*Setaria viridis* (L.) Beauv.) |
| pigweed | (*Amaranthus retroflexus* L.) |
| cocklebur | (*Xanthium pensylvanicum* Wallr.) |
| prickly sida | (*Sida spinosa* L.) |
| coffeeweed | (*Daubentonia texana* Pierce) |
| spurred anoda | (*Anoda cristata* (L.) Schlecht.) |
| rice | (*Oryza sativa* L.) |
| wild buckwheat | (*Polygonum convolvulus* L.) |
| sicklepod | (*Cassia obtusifolia* L.) |
| purslane | (*Portulaca oleracea* L.) |
| beggarweed | (*Desmodium tortuosum* (SW) DC.) |
| field Bindweed | (*Convolvulus arvenis* L.) |
| curled dock | (*Rumex crispus* L.) |
| radish | (*Raphanus sativus* L.) |
| wheat | (*Triticum aestivum* L.) |
| tomato | (*Lycopersicon esculentum* Mill. var. Tuckqueen or Heinz 1350) |
| nightshade | (*Solanum* spp.) |
| potato | (*Solanum tuberosum* L.) |

In preemergence primary evaluation tests chemicals of the invention in aqueous acetone solution were applied to seeded flats at rates equivalent to 4.48 kg active ingredient per hectare, and at submultiples thereof, namely 2.24 kg/ha, 1.12 kg/ha, and 0.56 kg/ha. Results of preemergence primary evaluation tests recorded two to three weeks after chemical application are summarized in Table 1. The 2,6-dichloro substituted benzoates are seen to be especially active in eliciting plant regulator responses. Additional preemergence primary evaluation results are recorded in Table 6; axillary growth stimulation of lima bean was noted.

In postemergence primary evaluation tests, chemicals of the invention in aqueous acetone solution were applied 10 to 14 days after planting. Results of primary evaluation tests, recorded two to three weeks after the chemical application, are summarized in Table 2. Activity against broad-leaved plants and inertness to grasses is striking. Additional postemergence primary evaluation results are recorded in Table 7; axillary growth stimulation of lima bean was noted.

EXAMPLE XXXIII

Plant Regulator Activity of Compound of Example I Applied Postemergence at Lower Rates Results of evaluation of plant regulator activity of the compound of Example I, applied to a variety of plant species at rates of 2.24 kg/ha, 1.12 kg/ha, 0.56 kg/ha, 0.28 kg/ha, and 0.14 kg/ha are summarized in Table 3, together with results obtained when the same species were left untreated. At the lowest level of application (0.14 kg/ha), morningglory, lettuce, pigweed, velvetleaf, ragweed, and beggarweed showed stunting and/or nastic responses. At the 0.28 kg/ha level, cocklebur, prickly sida, coffeeweed, spurred anoda, and wild buckwheat also began to show these responses. Acute decrease in plant height was manifested by cocklebur and ragweed as the level of chemical application was increased. Narrowing of leaves of pigweed ("strapping effect") was observed at all levels of application. Apical growth stimulation, that is, more than one leaf tip, was observed at higher levels of chemical application to cocklebur and velvetleaf, and stunting of growing tips was observed at higher levels of application to morningglory. These various plant regulator responses resulted in slight or moderate injury to growing plants, but in no case were plants observed to be killed by the treatment.

EXAMPLE XXXIV

Postemergence Plant Regulator Activity

Seeds of four species, radish, wheat, lima bean, and soybean were sown in separate 10-cm pots, sprinkled with fungicide, covered with a thin layer of soil (approximately 1 cm), and placed in the greenhouse, where they were watered regularly for two to three weeks, until growing plants had emerged. Twenty plants of each species were selected, four of which were sprayed with aqueous acetone solutions of the compound of Example I at each of four levels of application, corresponding to 0.56 kg/ha, 1.12 kg/ha, 2.24 kg/ha, and 4.48 kg/ha, and four of which were left untreated. All pots were returned to the greenhouse after treatment, and observed for plant regulator responses. Final observations, recorded 23, 31, 64, and 161 days after treatment (for radish, wheat, lima bean, and soybean, respectively), are summarized in Table 4. Slight increases in average weight of radish root, and a slight decrease in average height of wheat stalk were noted at the 0.56 kg/ha rate in comparison with untreated plants, but the differences were of doubtful significance. Lima beans were moderately to severely stunted at all rates, and bore no fruit. Nodes were telescoped into a compact structure. At the 0.56 kg/ha level branching was stimulated, and strapping of foliage was observed at the two lower rates of application.

Soybean nodes were telescoped into a compact structure, resulting in stunting. Soybeam vegetative production was reduced at all levels of chemical application in comparison with untreated plants. Fruit production was greatly reduced at the two higher levels, and slightly reduced at the 1.12 kg/ha level. At the 0.56 kg/ha level, however, fruit production was nearly twice that of the untreated plants, and at both the lower levels, the ratio of fruit weight to plant weight was nearly twice as great as the ratio for the untreated plants. Application of the compound of Example I at a proper rate is believed to result in diversion of the plant's energies from vegetative production to fruit production.

When the compound of Example I was applied to soybean plants sixty days after planting, and observations were recorded 130 days after treatment, the increase in ratio of pod weight/plant weight was less marked, suggesting that an optimum time for treatment may be somewhat earlier in the growth cycle of soybean.

EXAMPLE XXXV

Effect of Compound of Example I on Growth of Potato Plants and Tuber Production

Potatoes (var. Katahdin) were planted in 6-inch diameter pots and maintained in the greenhouse for 32 days, by which time plants averaged approximately 30 cm in height. Plants were sprayed with aqueous acetone solution of the compound of Example I at levels corresponding to 0.035 kg/ha, 0.07 kg/ha, 0.14 kg/ha, 0.28 kg/ha, and 0.56 kg/ha. There were four replicates at each level, and four replicates left untreated. Plants were harvested 28 days after treatment, and results are summarized in Table 5. At 0.07 kg/ha, 0.14 kg/ha, 0.28 kg/ha, and 0.56 kg/ha average plant heights were not significantly different from untreated plants, but average weight of tubers was approximately fifty percent greater than from untreated plants at 0.07 kg/ha, 0.28 kg/ha, and 0.56 kg/ha. The ratio of tuber weight to fresh weight of plants (cut off at ground level) was higher than four untreated plants at treatment levels of 0.07, 0.14, 0.28, and 0.56 kg/ha.

EXAMPLE XXXVI

Effect of Plant Regulator Compounds on Lima Bean Flowering and Pod Formation

Lima beans to which plant regulator compounds of the invention were applied two weeks after planting had produced flowers 28 days after treatment, at which time untreated plants had not flowered. The compounds of Examples XIII, XIV, XVII, XIX, and XXI showed flowering at an application rate corresponding to 0.07 kg/ha, and compounds of Examples I and XVIII showed flowering at a rate of 0.14 kg/ha. Plant injury remained slight (vigor rating: 4) at higher rates of application at which flowering was observed with several compounds. These results are summarized in Table 8.

Fifty-three days after treatment, these plants exhibited enhanced pod formation in comparison with untreated plants. Rates of application of 0.07 kg/ha and 0.14 kg/ha showed this effect in most cases, and the compounds of Examples XIX and XXI were effective at 0.56 kg/ha. These results are summarized in Table 9.

For application to plants, the active ingredients of this invention will not ordinarily be applied in undiluted form, but will be diluted or extended with an agriculturally acceptable, relatively inert material, here called a carrier, which may be liquid or solid. Thus the compounds of this invention may be utilized in diverse formulations prepared from agricultural adjuvants and agricultural carries to give the plant regulator compositions contemplated herein. The plant regulator compositions contain between about 0.01% and 95% active substituted benzoate together with between about 4% and 98.5% agriculturally acceptable carrier and between about 1% and 15% surface active agent by weight. As is well-known in the art, the formulation and mode of application of a plant regulator may affect the activity of the material in a given application. Thus, a compound of this invention may be formulated as an emulsifiable concentrate, as a resinous paste, as a flowable paste, as a wettable powder, as a solution, or as any of several other known types of formulations, depending on the desired mode of application. For regulation of established plant growth, sprays are most commonly used.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other non-volatile organic solvents.

Wettable powders, also useful formulations for plant regulators, are in the form of finely divided particles which disperse readily in water or other dispersants. The wettable powder is ultimately applied to the plant growth as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion. For example, a useful wettable powder formulation, designated 50 WP comprises 50 parts of the compound of Example I as active ingredient, 5 parts modified sodium lignosulfonate, 1 part of a solution of dioctyl ester of sodium sulfosuccinate (70% ester-30% mineral spirits as solvent), 30 parts of attapulgite clay, and 14 parts of synthetic precipitated hydrated silicon dioxide.

Typical wetting, dispersing or emulsifying agents used in agricultural formulations include, for example, the alkyl and alkylaryl sulfonates and sulfates and their sodium salts; polyethylene oxides; sulfonated oils; fatty acid esters of polyhydric alcohols; and other types of surface active agents, many of which are available in commerce. The surface-active agent, when used, normally comprises from 1% to 15% by weight of the herbicidal composition.

Resinous paste formulations are mixtures containing the active ingredient dispersed or suspended in an inert solid or semisolid organic substance obtained as an exudate of various plant or animal matter or prepared synthetically. Typical examples of resinous organic substances employed as carriers for the active ingredient include lanolin, asphalt, agar, and paraffin. These resinous paste formulations may contain between 0.01% and 50% of active ingredient, and may be applied to plants directly to the locus of desired application as the concentrated formulation or may first be diluted to a desired concentration of active ingredient by admixture with additional inert carrier substance.

Flowable paste formulations are mixtures of very finely divided active ingredients suspended in an emulsifying agent or other surface-active agent in the case of the highly concentrated flowable paste, or are suspensions in mixtures of water or other dispersing liquid with the emulsifying agent. These flowable paste concentrations may contain between 10% and 90% of active ingredient.

Other useful formulations include dusts which are admixtures of the active ingredient with finely divided solids such as talc, attapulgite clays, kieselguhr, and other organic and inorganic solids which act as dispersants and carriers for the active ingredients; these finely divided solids have an average particle size of less than 50 microns in diameter.

For application, these concentrated formulations are usually dispersed in water or other liquid carrier and applied as a spray to the plant growth to be treated. Or, in the case of solid formulations, application is carried out by dusting the formulation onto the plant growth to be regulated at a time when the normal leaf surface is in a condition such that the dust particles will adhere to the leaf surface.

The active plant regulator compounds of this invention may be formulated and/or applied with insecticides, fungicides, nematicides, other plant regulators, fertilizers, and other agricultural chemicals. In applying these active compounds, formulated alone or with other agricultural chemicals, an effective amount and concentration of the active substituted benzoate compound are of course employed. The amount constituting an effective amount is variable, depending on a number of factors such as the type of soil, the expected pattern of rainfall or irrigation, the plant species being treated and the time in the plant's growth cycle. Generally, a uniform application of between 0.02 and 2 kilograms per hectare will be employed, for example, 0.07 to 1.12 kilograms per hectare.

It is apparent that various modifications may be made in the formulation and application of the novel compositions of this invention, without departing from the inventive concept herein, as defined in the following claims.

TABLE 1

EVALUATION OF PREEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V[1] | K[2] | F[3] | V | K | F | V | K | F | V | K | F |

Experiment 1

I
| Lima Bean | 4 | 0 | 5 | 3 | 0 | 5 | 3 | 0 | 5 | 3 | 60 | 5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 4 | 80 | 0 | 0 | 100 | 12 | 0 | 100 | 12 |
| Mustard | 5 | 0 | 0 | 3 | 80 | 12 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 4 | 0 | 5 | 4 | 0 | 5 | 3 | 0 | 5 | 3 | 0 | 5 |
| Ragweed | 4 | 0 | 5 | 4 | 0 | 5 | 3 | 0 | 5 | 3 | 0 | 5 |
| Morningglory | 4 | 0 | 5 | 3 | 0 | 5 | 3 | 0 | 5 | 3 | 0 | 5 |
| Velvetleaf | 4 | 0 | 5 | 4 | 0 | 5 | 3 | 0 | 5 | 3 | 0 | 5 |
| Jimsonweed | 5 | 0 | 0 | 5 | 0 | 0 | 5 | 0 | 0 | 5 | 0 | 0 |
| Lambsquarter | 5 | 0 | 0 | 4 | 0 | 2 | 4 | 0 | 2 | 3 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |

II
| Lima Bean | 5 | 0 | 0 | 5 | 0 | 0 | 5 | 0 | 0 | 5 | 0 | 0 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 5 | 0 | 0 | 5 | 0 | 0 |
| Mustard | 5 | 0 | 0 | 5 | 0 | 0 | 5 | 0 | 0 | 5 | 0 | 0 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Ragweed | 5 | 0 | 0 | 5 | 0 | 0 | 5 | 0 | 0 | 5 | 0 | 0 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |

VII
| Lima Bean | 4 | 0 | 2 | 4 | 0 | 5 | 3 | 0 | 5 | 3 | 20 | 5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 80 | 12 | 0 | 100 | 12 | 0 | 100 | 12 | 5 | 0 | 0 |
| Mustard | 5 | 0 | 0 | 5 | 0 | 0 | 5 | 0 | 0 | 4 | 0 | 2 |
| Crabgrass | 5 | 0 | 0 | 5 | 0 | 0 | 5 | 0 | 0 | 5 | 0 | 0 |
| Soybean | 5 | 0 | 0 | 4 | 0 | 5 | 4 | 0 | 5 | 3 | 0 | 5 |
| Ragweed | 5 | 0 | 0 | 5 | 0 | 0 | 4 | 0 | 2 | 4 | 0 | 2 |
| Morningglory | 5 | 0 | 0 | 5 | 0 | 0 | 3 | 0 | 5 | 3 | 0 | 5 |
| Velvetleaf | 5 | 0 | 0 | 4 | 0 | 5 | 4 | 0 | 5 | 3 | 0 | 5 |
| Jimsonweed | 5 | 0 | 0 | 5 | 0 | 0 | 5 | 0 | 0 | 4 | 0 | 2 |
| Lambsquarter | 5 | 0 | 0 | 4 | 0 | 2 | 4 | 0 | 2 | 3 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |

IX
| Lima Bean | 4 | 0 | 2 | 4 | 0 | 2 | 3 | 0 | 2 | 3 | 20 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 0 | 100 | 12 | 4 | 30 | 12 | 3 | 95 | 12 |
| Mustard | 5 | 0 | 0 | 5 | 0 | 0 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 4 | 0 | 5 | 3 | 0 | 5 | 3 | 0 | 5 | 3 | 0 | 5 |
| Ragweed | 4 | 0 | 2 | 4 | 0 | 2 | 4 | 0 | 2 | 4 | 0 | 2 |
| Morningglory | 4 | 0 | 2 | 4 | 0 | 2 | 3 | 0 | 2 | 3 | 0 | 2 |
| Velvetleaf | 4 | 0 | 5 | 4 | 0 | 5 | 3 | 0 | 5 | 3 | 0 | 5 |
| Jimsonweed | 5 | 0 | 0 | 5 | 0 | 0 | 5 | 0 | 0 | 4 | 0 | 2 |
| Lambsquarter | 5 | 0 | 0 | 5 | 0 | 0 | 4 | 0 | 2 | 4 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |

X
| Lima Bean | 3 | 0 | 2 | 3 | 0 | 2 | 3 | 0 | 2 | 3 | 20 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 50 | 12 | 4 | 70 | 12 | 4 | 10 | 12 | 0 | 100 | 12 |
| Mustard | 5 | 0 | 0 | 5 | 0 | 0 | 4 | 0 | 2 | 3 | 50 | 2 |
| Crabgrass | 5 | 0 | 0 | 5 | 0 | 0 | 5 | 0 | 0 | 5 | 0 | 0 |
| Soybean | 4 | 0 | 5 | 4 | 0 | 5 | 3 | 0 | 5 | 3 | 0 | 5 |
| Ragweed | 4 | 0 | 2 | 4 | 0 | 2 | 4 | 0 | 2 | 4 | 0 | 2 |

TABLE 1-continued
EVALUATION OF PREEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V[1] | K[2] | F[3] | V | K | F | V | K | F | V | K | F |
| Morningglory | 5 | 0 | 0 | 4 | 0 | 2 | 3 | 0 | 2 | 3 | 0 | 2 |
| Velvetleaf | 3 | 0 | 5 | 3 | 0 | 5 | 3 | 0 | 5 | 3 | 0 | 5 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| XI | | | | | | | | | | | | |
| Lima Bean | 4 | 0 | 5 | 4 | 0 | 2 | 4 | 0 | 2 | 3 | 0 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 50 | 12 | 4 | 80 | 12 | 0 | 100 | 12 | 0 | 100 | 12 |
| Mustard | 5 | 0 | 0 | 4 | 0 | 2 | 3 | 50 | 2 | 4 | 60 | 2 |
| Crabgrass | 5 | 0 | 0 | 5 | 0 | 0 | 5 | 0 | 0 | 5 | 0 | 0 |
| Soybean | 3 | 0 | 5 | 3 | 0 | 5 | 3 | 0 | 5 | 3 | 0 | 5 |
| Ragweed | 4 | 0 | 2 | 4 | 0 | 2 | 4 | 0 | 2 | 4 | 0 | 2 |
| Morningglory | 3 | 0 | 2 | 3 | 0 | 2 | 3 | 0 | 2 | 3 | 0 | 2 |
| Velvetleaf | 4 | 0 | 5 | 4 | 0 | 5 | 3 | 0 | 5 | 3 | 0 | 5 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| XII | | | | | | | | | | | | |
| Lima Bean | 4 | 0 | 5 | 4 | 0 | 5 | 4 | 0 | 5 | 3 | 40 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 0 | 100 | 12 | 4 | 50 | 12 | 0 | 100 | 12 |
| Mustard | 5 | 0 | 0 | 5 | 0 | 0 | 5 | 0 | 0 | 5 | 0 | 0 |
| Crabgrass | 5 | 0 | 0 | 5 | 0 | 0 | 5 | 0 | 0 | 5 | 0 | 0 |
| Soybean | 3 | 0 | 5 | 3 | 0 | 5 | 3 | 0 | 5 | 3 | 0 | 5 |
| Ragweed | 4 | 0 | 2 | 4 | 0 | 2 | 4 | 0 | 2 | 3 | 0 | 2 |
| Morningglory | 5 | 0 | 0 | 4 | 0 | 2 | 4 | 0 | 2 | 3 | 0 | 2 |
| Velvetleaf | 4 | 0 | 5 | 4 | 0 | 5 | 3 | 0 | 5 | 3 | 0 | 5 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Experiment 2 | | | | | | | | | | | | |
| I | | | | | | | | | | | | |
| Lima Bean | 4 | 0 | 2 | 3 | 80 | 2 | 3 | 0 | 2 | 3 | 0 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 95 | 12 | 4 | 20 | 12 | 4 | 10 | 12 | 0 | 100 | 12 |
| Mustard | 5 | 0 | 0 | 5 | 0 | 0 | 5 | 0 | 0 | 3 | 0 | 2 |
| Crabgrass | 5 | 0 | 0 | 5 | 0 | 0 | 5 | 0 | 0 | 5 | 0 | 0 |
| Soybean | 3 | 0 | 2 | 3 | 0 | 2 | 3 | 0 | 2 | 3 | 0 | 2 |
| Ragweed | 3 | 0 | 2 | 3 | 0 | 2 | 3 | 0 | 2 | 3 | 0 | 2 |
| Morningglory | 3 | 0 | 2 | 3 | 0 | 2 | 3 | 0 | 2 | 3 | 0 | 2 |
| Velvetleaf | 4 | 0 | 5 | 4 | 0 | 5 | 3 | 0 | 5 | 3 | 0 | 5 |
| Jimsonweed | 5 | 0 | 0 | 5 | 0 | 0 | 5 | 0 | 0 | 4 | 0 | 2 |
| Lambsquarter | 4 | 0 | 2 | 4 | 0 | 2 | 4 | 0 | 2 | 3 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| III | | | | | | | | | | | | |
| Lima Bean | 4 | 0 | 2 | 4 | 0 | 5 | 4 | 0 | 5 | 4 | 0 | 5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 30 | 12 | 0 | 100 | 12 | 4 | 50 | 12 | 4 | 20 | 12 |
| Mustard | 4 | 0 | 2 | 4 | 0 | 2 | 4 | 0 | 2 | 5 | 0 | 0 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Ragweed | 5 | 0 | 0 | 5 | 0 | 0 | 5 | 0 | 0 | 5 | 0 | 0 |
| Morningglory | 5 | 0 | 0 | 5 | 0 | 0 | 5 | 0 | 0 | 4 | 0 | 2 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| IV | | | | | | | | | | | | |
| Lima Bean | 5 | 0 | 0 | 5 | 0 | 0 | 5 | 0 | 0 | 5 | 0 | 0 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 90 | 12 | 0 | 100 | 12 | 4 | 50 | 12 | 4 | 30 | 12 |
| Mustard | 4 | 0 | 2 | 4 | 0 | 2 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |

TABLE 1-continued
EVALUATION OF PREEMERGENCE PLANT REGULATOR ACTIVITY OF (SUBSTITUTED)METHYL OPTIONALLY-SUBSTITUTED BENZOATES

| Compound of Example Plant Species | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| | V[1] | K[2] | F[3] | V | K | F | V | K | F | V | K | F |
| Ragweed | 5 | 0 | 0 | 5 | 0 | 0 | 5 | 0 | 0 | 5 | 0 | 0 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| V | | | | | | | | | | | | |
| Lima Bean | 5 | 0 | 0 | 5 | 0 | 0 | 5 | 0 | 0 | 5 | 0 | 0 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 30 | 12 | 4 | 10 | 12 | 4 | 50 | 12 | 0 | 100 | 12 |
| Mustard | 5 | 0 | 0 | 5 | 0 | 0 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Ragweed | 5 | 0 | 0 | 5 | 0 | 0 | 5 | 0 | 0 | 5 | 0 | 0 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| VI | | | | | | | | | | | | |
| Lima Bean | 4 | 0 | 2 | 4 | 0 | 2 | 4 | 0 | 2 | 4 | 0 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 4 | 90 | 12 | 4 | 90 | 12 |
| Mustard | 5 | 0 | 0 | 5 | 0 | 0 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Ragweed | 5 | 0 | 0 | 5 | 0 | 0 | 5 | 0 | 0 | 5 | 0 | 0 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 4 | 0 | 2 |
| Lambsquarter | 5 | 0 | 0 | 5 | 0 | 0 | 5 | 0 | 0 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| I | | | | | | | | | | | | |
| Lima Bean | 3 | 0 | 2 | 3 | 0 | 2 | 3 | 0 | 2 | 3 | 0 | 2/5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 5 | 0 | 0 | 4 | 0 | 2 |
| Velvetleaf | 4 | 0 | 5 | 4 | 0 | 2/5 | 3 | 0 | 2/5 | 3 | 0 | 2/5 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Nightshade | 5 | 0 | 0 | 5 | 0 | 0 | 5 | 0 | 0 | 5 | 0 | 0 |
| Mustard | 4 | 0 | 2 | 4 | 0 | 2 | 4 | 0 | 2/5 | 3 | 0 | 2/5 |
| Crabgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Tomato | 5 | 0 | 0 | 5 | 0 | 0 | 4 | 0 | 2 | 4 | 0 | 2 |
| Soybean | 4 | 0 | 2/5 | 3 | 0 | 2/5 | 3 | 0 | 2/5 | 3 | 0 | 2/5 |
| Ragweed | 4 | 0 | 2 | 4 | 0 | 2 | 4 | 0 | 2 | 3 | 0 | 2 |
| Morningglory | 4 | 0 | 2 | 4 | 0 | 2 | 4 | 0 | 2 | 4 | 0 | 2 |
| Wild Buckwheat | 4 | 0 | 5 | 4 | 0 | 5 | 4 | 0 | 5 | 3 | 0 | 5 |
| VIII | | | | | | | | | | | | |
| Lima Bean | 3 | 0 | 2/5 | 3 | 0 | 2 | 3 | 0 | 2 | 3 | 0 | 2/5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 5 | 0 | 0 | 5 | 0 | 0 |
| Velvetleaf | 4 | 0 | 5 | 4 | 0 | 5 | 3 | 0 | 5/2 | 3 | 0 | 5 |
| Lambsquarter | 5 | 0 | 0 | 5 | 0 | 0 | 4 | 0 | 2 | 4 | 0 | 2 |
| Barnyardgrass | 5 | 0 | 0 | 5 | 0 | 0 | 5 | 0 | 0 | 5 | 0 | 0 |
| Nightshade | 5 | 0 | 0 | 5 | 0 | 0 | 5 | 0 | 0 | 5 | 0 | 0 |
| Mustard | 4 | 0 | 5 | 4 | 0 | 5 | 4 | 0 | 5 | 4 | 0 | 5 |
| Crabgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Tomato | 5 | 0 | 0 | 5 | 0 | 0 | 4 | 0 | 2 | 4 | 0 | 2 |
| Soybean | 3 | 0 | 2/5 | 3 | 0 | 2/5 | 3 | 0 | 2/5 | 3 | 0 | 2/5 |
| Ragweed | 4 | 0 | 2 | 4 | 0 | 2 | 4 | 0 | 2 | 4 | 0 | 2 |
| Morningglory | 4 | 0 | 2/5 | 4 | 0 | 2/5 | 4 | 0 | 2/5 | 4 | 0 | 2/5 |
| Wild Buckwheat | 0 | 100 | 12 | 4 | 0 | 2 | 4 | 0 | 5/2 | 4 | 0 | 5 |
| XV | | | | | | | | | | | | |
| Lima Bean | 4 | 0 | 2/5 | 3 | 0 | 2/5 | 3 | 0 | 2/5 | 3 | 0 | 2/5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |

TABLE 1-continued
EVALUATION OF PREEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V[1] | K[2] | F[3] | V | K | F | V | K | F | V | K | F |
| Lettuce | 5 | 0 | 0 | 5 | 0 | 0 | 5 | 0 | 0 | 5 | 0 | 0 |
| Velvetleaf | 5 | 0 | 0 | 5 | 0 | 0 | 4 | 0 | 5 | 4 | 0 | 5 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Nightshade | 5 | 0 | 0 | 5 | 0 | 0 | 5 | 0 | 0 | 4 | 0 | 5 |
| Mustard | 5 | 0 | 0 | 5 | 0 | 0 | 5 | 0 | 0 | 5 | 0 | 0 |
| Crabgrass | 5 | 0 | 0 | 5 | 0 | 0 | 5 | 0 | 0 | 3 | 50 | 2 |
| Green Foxtail | 5 | 0 | 0 | 5 | 0 | 0 | 5 | 0 | 0 | 5 | 0 | 0 |
| Tomato | 5 | 0 | 0 | 5 | 0 | 0 | 5 | 0 | 0 | 4 | 0 | 2 |
| Soybean | 4 | 0 | 2/5 | 4 | 0 | 2/5 | 4 | 0 | 2/5 | 3 | 0 | 2/5 |
| Ragweed | 5 | 0 | 0 | 4 | 0 | 2 | 4 | 0 | 2 | 4 | 0 | 2 |
| Morningglory | 4 | 0 | 2/5 | 4 | 0 | 2/5 | 4 | 0 | 2/5 | 4 | 0 | 2/5 |
| Wild Buckwheat | 4 | 0 | 5 | 4 | 0 | 5 | 4 | 0 | 5 | 3 | 0 | 5 |

1. V = Vigor:
5 = Plants normal.
4 = Slight Injury, plants will or have already recovered.
3 = Moderate injury; plants expected to recover.
2 = Moderate to severe injury; plants are not expected to recover.
1 = Severe injury; plants will not recover.
0 = Dead plant.
2. K = Percent kill.
3. F = Footnote code designation:
1 = Necrosis
2 = Stunted
3 = Desiccation
4 = Axillary Growth Stimulation
5 = Nastic responses
6 = Necrotic spots
7 = Growth stimulation
8 = Defoliant
9 = Chlorosis
10 = Intumescence
11 = Suspected germination failure
12 = Stand may have been affected by non-chemical factors

TABLE 2
EVALUATION OF POSTEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V | K | F | V | K | F | V | K | F | V | K | F |
| *Experiment 1* | | | | | | | | | | | | |
| I | | | | | | | | | | | | |
| Lima Bean | 3 | 0 | 2 | 3 | 0 | 2 | 3 | 0 | 2 | 3 | 20 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 0 | 100 | 12 | 0 | 100 | 12 | 0 | 100 | 12 |
| Mustard | 4 | 0 | 2 | 4 | 0 | 2 | 3 | 0 | 2 | 3 | 0 | 5 |
| Crabgrass | 5 | 0 | 0 | 5 | 0 | 0 | 5 | 0 | 0 | 5 | 0 | 0 |
| Soybean | 4 | 0 | 5 | 3 | 0 | 5 | 3 | 0 | 5 | 3 | 0 | 5 |
| Ragweed | 3 | 0 | 2 | 3 | 0 | 2 | 3 | 0 | 2 | 3 | 0 | 5 |
| Morningglory | 4 | 0 | 2 | 4 | 0 | 2 | 3 | 0 | 2 | 3 | 0 | 2 |
| Velvetleaf | 4 | 0 | 5 | 3 | 0 | 5 | 3 | 0 | 5 | 3 | 0 | 5 |
| Jimsonweed | 4 | 0 | 2 | 3 | 0 | 2 | 3 | 0 | 2 | 3 | 0 | 2 |
| Lambsquarter | 3 | 0 | 2 | 3 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| II | | | | | | | | | | | | |
| Lima Bean | 4 | 0 | 5 | 4 | 0 | 5 | 4 | 0 | 5 | 3 | 0 | 5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 4 | 70 | 12 | 0 | 100 | 12 | 0 | 100 | 12 |
| Mustard | 5 | 0 | 0 | 5 | 0 | 0 | 4 | 0 | 2 | 3 | 0 | 2 |
| Crabgrass | 5 | 0 | 0 | 5 | 0 | 0 | 5 | 0 | 0 | 5 | 0 | 0 |
| Soybean | 3 | 0 | 10 | 4 | 0 | 5 | 4 | 0 | 5 | 4 | 0 | 5 |
| Ragweed | 3 | 0 | 2 | 4 | 0 | 2 | 5 | 0 | 0 | 5 | 0 | 0 |
| Morningglory | 4 | 0 | 5 | 4 | 0 | 5 | 4 | 0 | 5 | 4 | 0 | 5 |
| Velvetleaf | 3 | 0 | 5 | 4 | 0 | 5 | 4 | 0 | 5 | 4 | 0 | 5 |
| Jimsonweed | 4 | 0 | 2 | 5 | 0 | 0 | 5 | 0 | 0 | 5 | 0 | 0 |
| Lambsquarter | 3 | 0 | 2 | 4 | 0 | 2 | 4 | 0 | 2 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| VII | | | | | | | | | | | | |
| Lima Bean | 4 | 0 | 2 | 3 | 0 | 2 | 3 | 0 | 2 | 3 | 0 | 2 |

TABLE 2-continued
EVALUATION OF POSTEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V | K | F | V | K | F | V | K | F | V | K | F |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 4 | 80 | 12 | 0 | 100 | 12 | 0 | 100 | 12 |
| Mustard | 5 | 0 | 0 | 4 | 0 | 2 | 4 | 0 | 2 | 3 | 0 | 2 |
| Crabgrass | 5 | 0 | 0 | 5 | 0 | 0 | 5 | 0 | 0 | 5 | 0 | 0 |
| Soybean | 3 | 0 | 5 | 3 | 0 | 5 | 3 | 0 | 5 | 3 | 0 | 5 |
| Ragweed | 4 | 0 | 2 | 4 | 0 | 2 | 3 | 0 | 2 | 3 | 0 | 5 |
| Morningglory | 4 | 0 | 5 | 4 | 0 | 5 | 4 | 0 | 5 | 3 | 0 | 2 |
| Velvetleaf | 4 | 0 | 5 | 4 | 0 | 5 | 3 | 0 | 5 | 3 | 0 | 5 |
| Jimsonweed | 5 | 0 | 0 | 4 | 0 | 2 | 3 | 0 | 2 | 3 | 0 | 5 |
| Lambsquarter | 3 | 0 | 2 | 3 | 0 | 2 | 3 | 0 | 2 | 2 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| XII | | | | | | | | | | | | |
| Lima Bean | 3 | 0 | 5 | 3 | 0 | 2 | 3 | 0 | 2 | 3 | 0 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 0 | 100 | 12 | 0 | 100 | 12 | 4 | 0 | 5 |
| Mustard | 5 | 0 | 0 | 4 | 0 | 2 | 3 | 0 | 2 | 3 | 0 | 5 |
| Crabgrass | 5 | 0 | 0 | 5 | 0 | 0 | 5 | 0 | 0 | 5 | 0 | 0 |
| Soybean | 3 | 0 | 5 | 3 | 0 | 10 | 3 | 0 | 10 | 3 | 0 | 10 |
| Ragweed | 4 | 0 | 2 | 3 | 0 | 2 | 3 | 0 | 2 | 3 | 0 | 5 |
| Morningglory | 4 | 0 | 5 | 4 | 0 | 5 | 3 | 0 | 5 | 3 | 0 | 2 |
| Velvetleaf | 4 | 0 | 5 | 3 | 0 | 5 | 3 | 0 | 5 | 3 | 0 | 5 |
| Jimsonweed | 5 | 0 | 0 | 3 | 0 | 2 | 3 | 0 | 2 | 3 | 0 | 5 |
| Lambsquarter | 4 | 0 | 2 | 4 | 0 | 2 | 3 | 0 | 2 | 3 | 0 | 5 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Experiment 2* | | | | | | | | | | | | |
| I | | | | | | | | | | | | |
| Lima Bean | 3 | | 2 | 3 | 0 | 2 | 3 | 0 | 2 | 0 | 100 | 0 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 0 | 100 | 12 | 0 | 100 | 12 | 0 | 100 | 12 | 0 | 100 | 12 |
| Mustard | 5 | 0 | 0 | 4 | 0 | 2 | 3 | 0 | 2 | 3 | 0 | 2 |
| Crabgrass | 5 | 0 | 0 | 5 | 0 | 0 | 5 | 0 | 0 | 5 | 0 | 0 |
| Soybean | 4 | 0 | 5 | 4 | 0 | 5 | 3 | 0 | 5 | 3 | 0 | 5 |
| Ragweed | 0 | 100 | 11 | 0 | 100 | 11 | 0 | 100 | 11 | 0 | 100 | 11 |
| Morningglory | 4 | 0 | 5 | 4 | 0 | 5 | 3 | 0 | 5 | 3 | 0 | 5 |
| Velvetleaf | 4 | 0 | 5 | 3 | 0 | 5 | 3 | 0 | 5 | 3 | 0 | 5 |
| Jimsonweed | 5 | 0 | 0 | 5 | 0 | 0 | 5 | 0 | 0 | 3 | 0 | 2 |
| Lambsquarter | 4 | 0 | 2 | 4 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| III | | | | | | | | | | | | |
| Lima Bean | 5 | 0 | 0 | 5 | 0 | 0 | 5 | 0 | 0 | 5 | 0 | 0 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 90 | 12 | 4 | 90 | 12 | 4 | 20 | 12 | 4 | 95 | 12 |
| Mustard | 5 | 0 | 0 | 4 | 0 | 2 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Ragweed | 0 | 100 | 11 | 0 | 100 | 11 | 0 | 100 | 11 | 0 | 100 | 11 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 4 | 0 | 2 | 4 | 0 | 2 |
| Jimsonweed | 5 | 0 | 0 | 5 | 0 | 0 | 5 | 0 | 0 | 5 | 0 | 2 |
| Lambsquarter | 5 | 0 | 0 | 5 | 0 | 0 | 5 | 0 | 0 | 4 | 0 | 2 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| IV | | | | | | | | | | | | |
| Lima Bean | 5 | 0 | 0 | 5 | 0 | 0 | 5 | 0 | 0 | 4 | 0 | 2 |
| Corn | 5 | 0 | 0 | 5 | 0 | 0 | 5 | 0 | 0 | 5 | 0 | 0 |
| Wild Oats | 5 | 0 | 0 | 5 | | 0 | 5 | 0 | 0 | 5 | 0 | 0 |
| Lettuce | 0 | 100 | 12 | 0 | 100 | 12 | 0 | 100 | 12 | 4 | 30 | 12 |
| Mustard | 5 | 0 | 0 | 4 | 0 | 2 | 4 | 0 | — | 4 | 0 | 2 |
| Crabgrass | 5 | 0 | 0 | 5 | 0 | 0 | 5 | 0 | 0 | 5 | 0 | 0 |
| Soybean | 5 | 0 | 0 | 5 | 0 | 0 | 5 | 0 | 0 | 5 | 0 | 0 |
| Ragweed | 0 | 100 | 11 | 5 | 0 | 0 | 0 | 100 | 11 | 0 | 100 | 11 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| V | | | | | | | | | | | | |

TABLE 2-continued
EVALUATION OF POSTEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V | K | F | V | K | F | V | K | F | V | K | F |
| Lima Bean | 5 | 0 | 0 | 5 | 0 | 0 | 5 | 0 | 0 | 5 | 0 | 0 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 4 | 50 | 12 | 0 | 100 | 12 | 4 | 80 | 12 | 0 | 100 | 12 |
| Mustard | 4 | 0 | 2 | 4 | 0 | 2 | 4 | 0 | 2 | 4 | 0 | 2 |
| Crabgrass | 5 | 0 | 0 | 5 | 0 | 0 | 5 | 0 | 0 | 5 | 0 | 0 |
| Soybean | 5 | 0 | | 5 | 0 | 0 | 5 | 0 | 0 | 5 | 0 | 0 |
| Ragweed | 0 | 100 | 11 | 0 | 100 | 11 | 0 | 100 | 11 | 0 | 100 | 11 |
| Morningglory | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Jimsonweed | 5 | 0 | 0 | 5 | 0 | 0 | 5 | 0 | 0 | 5 | 0 | 0 |
| Lambsquarter | 5 | 0 | 0 | 5 | 0 | 0 | 5 | 0 | 0 | 5 | 0 | 0 |
| Barnyardgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| VI | | | | | | | | | | | | |
| Lima Bean | | | | | | | 5 | 0 | 0 | 5 | 0 | 0 |
| Corn | | | | | | | 5 | 0 | 0 | 5 | 0 | 0 |
| Wild Oats | | | | | | | 5 | 0 | 0 | 5 | 0 | 0 |
| Lettuce | | | | | | | 0 | 100 | 12 | 0 | 100 | 12 |
| Mustard | | | | | | | 3 | 0 | 2 | 3 | 0 | 2 |
| Crabgrass | | | | | | | 5 | 0 | 0 | 5 | 0 | 0 |
| Soybean | | | | | | | 5 | 0 | 0 | 5 | 0 | 0 |
| Ragweed | | | | | | | 0 | 100 | 11 | 0 | 100 | 11 |
| Morningglory | | | | | | | 5 | 0 | 0 | 5 | 0 | 0 |
| Velvetleaf | | | | | | | 5 | 0 | 0 | 5 | 0 | 0 |
| Jimsonweed | | | | | | | 5 | 0 | 0 | 5 | 0 | 0 |
| Lambsquarter | | | | | | | 5 | 0 | 0 | 5 | 0 | 0 |
| Barnyardgrass | | | | | | | 5 | 0 | | 5 | 0 | 0 |
| Green Foxtail | | | | | | | 5 | 0 | 0 | 5 | 0 | 0 |
| *Exmperiment 3* | | | | | | | | | | | | |
| I | | | | | | | | | | | | |
| Lima Bean | 3 | 0 | 2 | 3 | 0 | 2/1 | 3 | 0 | 2/1 | 3 | 0 | 2/1 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 5 | 0 | 0 | 4 | 0 | 2 |
| Velvetleaf | 4 | 0 | 5 | 4 | 0 | 5 | 3 | 0 | 5/2 | 3 | 0 | 5/2 |
| Lambsquarter | 4 | 0 | 2 | 4 | 0 | 2 | 4 | 0 | 2 | 3 | 0 | 2/5 |
| Barnyardgrass | 5 | 0 | 0 | 5 | 0 | 0 | 5 | 0 | 0 | 5 | 0 | 0 |
| Nightshade | 5 | 0 | 0 | 5 | 0 | | 4 | 0 | 2 | 4 | 0 | 5 |
| Mustard | 4 | 0 | 1 | 3 | 0 | 2 | 3 | 0 | 2 | 3 | 0 | 2/1 |
| Crabgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Tomato | 5 | 0 | 0 | 5 | 0 | 0 | 5 | 0 | 0 | 4 | 0 | 2 |
| Soybean | 4 | 0 | 2/5 | 4 | 0 | 2/5 | 4 | 0 | 2/5 | 3 | 0 | 2/5 |
| Ragweed | 4 | 0 | 2 | 4 | 0 | 2 | 4 | 0 | 2 | 4 | 0 | 2 |
| Morningglory | 4 | 0 | 2 | 4 | 0 | 2 | 4 | 0 | 2/5 | 4 | 0 | 2/5 |
| Wild Buckwheat | 4 | 0 | 5 | 4 | 0 | 2 | 4 | 0 | 2 | 4 | 0 | 2 |
| VIII | | | | | | | | | | | | |
| Lima Bean | 4 | 0 | 2/5 | 4 | 0 | 2/5 | 3 | 0 | 2 | 3 | 0 | 2 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 4 | 0 | 2 | 4 | 0 | 2 |
| Velvetleaf | 4 | 0 | 5 | 4 | 0 | 5 | 4 | 0 | 5 | 4 | 0 | 5 |
| Lambsquarter | 5 | 0 | 0 | 5 | 0 | 0 | 4 | 0 | 2 | 4 | 0 | 2 |
| Barnyardgrass | 5 | 0 | 0 | 5 | 0 | 0 | 5 | 0 | 0 | 5 | 0 | 0 |
| Nightshade | 5 | 0 | 0 | 5 | 0 | 0 | 5 | 0 | 0 | 4 | 0 | 5 |
| Mustard | 5 | 0 | 0 | 5 | 0 | 0 | 4 | 0 | 2 | 4 | 0 | 2 |
| Crabgrass | 5 | 0 | 0 | 5 | 0 | 0 | 5 | 0 | 0 | 5 | 0 | 0 |
| Green Foxtail | 5 | 0 | | 5 | 0 | 0 | 5 | 0 | 0 | 5 | 0 | 0 |
| Tomato | 5 | 0 | 0 | 4 | 0 | 2 | 4 | 0 | 2 | 4 | 0 | 2 |
| Soybean | 4 | 0 | 2/5 | 4 | 0 | 2/5 | 3 | 0 | 2/5 | 3 | 0 | 2/5 |
| Ragweed | 4 | 0 | 2 | 4 | 0 | 2 | 4 | 0 | 2 | 4 | 0 | 2 |
| Morningglory | 4 | 0 | 2 | 4 | 0 | 2 | 4 | 0 | 2 | | | |
| Wild Buckwheat | 5 | 0 | 0 | 5 | 0 | 0 | 5 | 0 | 0 | 4 | 0 | 5 |
| XV | | | | | | | | | | | | |
| Lima Bean | 4 | 0 | 2 | 4 | 0 | 2/6 | 4 | 0 | 2/5 | 3 | 0 | 1/5 |
| Corn | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Lettuce | 5 | 0 | 0 | 5 | 0 | 0 | 4 | 0 | 2 | 4 | 0 | 2 |
| Velvetleaf | 4 | 0 | 5 | 4 | | 5 | 4 | 0 | 5 | 3 | 0 | 2/5 |
| Lambsquarter | 5 | 0 | 0 | 5 | 0 | 0 | 4 | 0 | 2 | 3 | 0 | 2 |
| Barnyardgrass | 5 | 0 | 0 | 5 | 0 | 0 | 5 | 0 | 0 | 5 | 0 | 0 |
| Nightshade | 5 | 0 | 0 | 5 | 0 | 0 | 4 | 0 | 5 | 4 | 0 | 2 |
| Mustard | 5 | 0 | 0 | 5 | 0 | 0 | 4 | 0 | 5 | 3 | 0 | 2 |

TABLE 2-continued

EVALUATION OF POSTEMERGENCE PLANT REGULATOR ACTIVITY OF (SUBSTITUTED)METHYL OPTIONALLY-SUBSTITUTED BENZOATES

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V | K | F | V | K | F | V | K | F | V | K | F |
| Crabgrass | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Tomato | 5 | 0 | 0 | 5 | 0 | 0 | 4 | 0 | 2 | 3 | 0 | 2 |
| Soybean | 4 | 0 | 2/5 | 4 | 0 | 2/5/6 | 4 | 0 | 2/5/6 | 3 | 0 | 1/5/2 |
| Ragweed | 4 | 0 | 2 | 4 | 0 | 2 | 4 | 0 | 2 | 4 | 0 | 2 |
| Morningglory | 4 | 0 | 2/5 | 4 | 0 | 2/6 | 4 | 0 | 2/5/6 | 3 | 0 | 2/1 |
| Wild Buckwheat | 5 | 0 | 0 | 4 | 0 | 5 | 4 | 0 | 2 | 4 | 0 | 2 |

*See Table 1 for definition of Vigor (V) and Footnote (F) code designation; K refers to percent kill.

TABLE 3

PLANT REGULATOR ACTIVITY* OF COMPOUND OF EXAMPLE I APPLIED POSTEMERGENCE TO SEVERAL PLANT SPECIES

| Plant Species | Rate of Application (kilograms/hectare) | | | | | | | | | | | | | | | | | |
|---|---|---|---|---|---|---|---|---|---|---|---|---|---|---|---|---|---|---|
| | 0.14 | | | 0.28 | | | 0.56 | | | 1.12 | | | 2.24 | | | Untreated | | |
| | V | K | F | V | K | F | V | K | F | V | K | F | V | K | F | V | K | F |
| Wheat | 5 | 0 | 0 | 5 | 0 | 0 | 5 | 0 | 0 | 5 | 0 | 0 | 4 | 0 | 2 | 5 | 0 | 0 |
| Morningglory[1] | 4 | 0 | 2 | 4 | 0 | 2 | 3 | 0 | 5/2 | 3 | 0 | 5/2 | 3 | 0 | 5/2 | 5 | 0 | 0 |
| Lettuce | 3 | 0 | 2 | 3 | 0 | 2 | 3 | 0 | 2 | 3 | 0 | 5/2 | 3 | 0 | 5/2 | 5 | 0 | 0 |
| Pigweed[2] | 4 | 0 | 5/2 | 4 | 0 | 5/2 | 4 | 0 | 5/2 | 3 | 0 | 5/2 | 3 | 0 | 5/2 | 5 | 0 | 0 |
| Cocklebur[3,4] | 5 | 0 | 0 | 4 | 0 | 5 | 3 | 0 | 5/2 | 3 | 0 | 5/2 | 3 | 0 | 5/2 | 5 | 0 | 0 |
| Prickly Sida[1] | 5 | 0 | 0 | 4 | 0 | 5 | 3 | 0 | 5 | 3 | 0 | 5/2 | 3 | 0 | 5/2 | 5 | 0 | 0 |
| Coffeeweed | 5 | 0 | 0 | 4 | 0 | 5 | 4 | 0 | 5 | 3 | 0 | 5/2 | 3 | 0 | 5 | 5 | 0 | 0 |
| Velvetleaf[4] | 4 | 0 | 5/2 | 4 | 0 | 5/2 | 4 | 0 | 5/2 | 3 | 0 | 5/2 | 3 | 0 | 5/2 | 5 | 0 | 0 |
| Spurred Anoda | 5 | 0 | 0 | 4 | 0 | 5 | 4 | 0 | 5 | 4 | 0 | 5/2 | 3 | 0 | 5/2 | 5 | 0 | 0 |
| Penns. Smartweed | 5 | 0 | 0 | 5 | 0 | 0 | 5 | 0 | 0 | 5 | 0 | 0 | 5 | 0 | 0 | 5 | 0 | 0 |
| Rice | 5 | 0 | 0 | 5 | 0 | 0 | 5 | 0 | 0 | 5 | 0 | 0 | 5 | 0 | 0 | 5 | 0 | 0 |
| Wild Buckwheat | 5 | 0 | 0 | 4 | 0 | 2 | 3 | 0 | 5/2 | 3 | 0 | 5/2 | 3 | 0 | 5/2 | 5 | 0 | 0 |
| Sicklepod | 5 | 0 | 0 | 5 | 0 | 0 | 5 | 0 | 0 | 4 | 0 | 5/2 | 3 | 0 | 5/2 | 5 | 0 | 0 |
| Purslane | 5 | 0 | 0 | 5 | 0 | 0 | 5 | 0 | 0 | 5 | 0 | 0 | 3 | 0 | 5/2 | 5 | 0 | 0 |
| Ragweed[5] | 4 | 0 | 2 | 4 | 0 | 5/2 | 3 | 0 | 5/2 | 3 | 0 | 5/2 | 2 | 30 | 5/2 | 5 | 0 | 0 |
| Beggarweed | 3 | 0 | 5/2 | 3 | 0 | 5/2 | 3 | 0 | 5/2 | 3 | 0 | 5/2 | 2 | 0 | 5/2 | 5 | 0 | 0 |
| Bindweed | 5 | 0 | 0 | 5 | 0 | 0 | 4 | 0 | 5 | 4 | 0 | 5 | 3 | 20 | 2/5/12 | 5 | 0 | 0 |
| Curled Dock | 4 | 80 | 12 | 5 | 0 | 0 | 5 | 0 | 0 | 5 | 0 | 0 | 5 | 0 | 0 | 5 | 0 | 0 |

*Definitions of V, F, and K designations follow Table 1.
[1] Stunting of growing tips at higher rates.
[2] Strapping effect (narrowing of leaves) of foliage at all rates.
[3] Cocklebur showed marked decrease in height as rate increased; as follows:

| Rate (kg/ha) | Average height (cm) |
|---|---|
| 0.14 | 7.5 |
| 0.28 | 7.5 |
| 0.56 | 5.0 |
| 1.12 | 4.0 |
| 2.24 | 2.5 |
| Untreated | 8.0 |

[4] At higher rates apical growth stimulation (more than one leaf tip) was exhibited.
[5] Ragweed showed marked decrease in height as rate increased, as follows:

| Rate (kg/ha) | Average height (cm) |
|---|---|
| 0.14 | 9.5 |
| 0.28 | 8.0 |
| 0.56 | 5.5 |
| 1.12 | 4.5 |
| 2.24 | 3.5 |
| Untreated | 9.5 |

TABLE 4

PLANT REGULATOR ACTIVITY OF COMPOUND OF EXAMPLE I APPLIED POSTEMERGENCE TO RADISH, WHEAT, LIMA BEAN, SOYBEAN

Radish - 23 days after treatment

| Rate (kg/ha) | Average* Weight (grams) | |
|---|---|---|
| | Shoots | Roots |
| 0.56 | 5.1 | 10.2 |
| 1.12 | 4.9 | 7.1 |
| 2.24 | 5.8 | 5.5 |
| 4.48 | 5.5 | 3.3 |
| Untreated | 5.1 | 9.5 |

Wheat - 31 days after treatment

| Rate (kg/ha) | Average* Height (cm) |
|---|---|
| 0.56 | 23.0 |
| 1.12 | 26.8 |
| 2.24 | 23.8 |
| 4.48 | 26.0 |
| Untreated | 24.5 |

Lima Bean - 64 days after treatment

| Rate (kg/ha) | Average* Height (cm) | Average No. of Pods |
|---|---|---|
| 0.56[1] | 9.0 | 0 |
| 1.12[2] | 6.5 | 0 |
| 2.24[3] | 6.0 | 0 |
| 4.48[4] | 6.4 | 0 |
| Untreated | 15.3 | 1.9 |

TABLE 4-continued

PLANT REGULATOR ACTIVITY OF COMPOUND OF EXAMPLE I APPLIED POSTEMERGENCE TO RADISH, WHEAT, LIMA BEAN, SOYBEAN

Soybean - 161 days after treatment

| Rate (kg/ha) | Height (cm) | Pods (No.) | Plant Wt(g) | Pod Wt(g) | Ratio Pod Wt/ Plant Wt |
|---|---|---|---|---|---|
| 0.56 | 10.8 | 18.0 | 20.21 | 8.03 | 0.27 |
| 1.12 | 7.9 | 8.0 | 13.30 | 3.34 | 0.25 |
| 2.24 | 6.8 | 3.6 | 6.47 | 1.17 | 0.18 |
| 4.48 | 5.6 | 1.3 | 2.04 | 0.21 | 0.10 |
| Control | 15.8 | 20.0 | 33.03 | 4.49 | 0.14 |

*Average of four replicates in each case.
[1] 0.56 kg/ha - strapping of foliage; severe stunting of new growth; stimulated branching.
[2] 1.12 kg/ha - severe stunting and strapping of foliage; marginal necrosis.
[3] 2.24 kg/ha - complete inhibition of terminal growth; severe intumescence at growing point; necrotic spots and margins.
[4] 4.48 kg/ha - tumorous growth on upper surfaces of primary leaves; severe intumescence; severe necrosis of primary leaves.

TABLE 5

Effect on Potato of Compound of Example I Applied 32 Days After Planting

| Rate (kg/ha) | Average* - 28 Days After Treatment | | | | Ratio Tuber Wt/ Plant Wt |
|---|---|---|---|---|---|
| | Height (cm) | Tubers (No.) | Plant Wt(g) | Tuber Wt(g) | |
| 0.035 | 64.8 | 4.5 | 43.5 | 20.9 | 0.48 |
| 0.07 | 58.7 | 3.5 | 43.3 | 31.7 | 0.73 |
| 0.14 | 56.3 | 4.5 | 38.2 | 24.2 | 0.63 |
| 0.28 | 59.9 | 4.0 | 43.9 | 34.3 | 0.78 |
| 0.56 | 58.7 | 3.5 | 38.2 | 32.7 | 0.86 |
| Untreated | 57.3 | 4.5 | 44.3 | 22.3 | 0.50 |

*Average of four replicates in each case.

TABLE 6

Evaluation of Preemergence Plant Regulator Activity of Substituted Benzoates

Experiment 1*

| Compound of Example / Plant Species | 0.56 V | 0.56 K | 0.56 F | 1.12 V | 1.12 K | 1.12 F | 2.24 V | 2.24 K | 2.24 F | 4.48 V | 4.48 K | 4.48 F |
|---|---|---|---|---|---|---|---|---|---|---|---|---|
| I | | | | | | | | | | | | |
| Lima Bean | 3 | 0 | 4,2,5 | 3 | 0 | 2 | 3 | 0 | 2 | 2 | 60 | 2 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 4 | 0 | 2 | 4 | 0 | 2 |
| Green Foxtail | 5 | 0 | 0 | 5 | 0 | 0 | 4 | 10 | 0 | 5 | 0 | 0 |
| Velvetleaf | 4 | 0 | 5 | 4 | 0 | 5 | 3 | 0 | 5 | 3 | 0 | 5 |
| Tomato | 4 | 0 | 2 | 4 | 0 | 2 | 4 | 0 | 2 | 3 | 0 | 5 |
| Bindweed | 3 | 0 | 2 | 3 | 0 | 2 | 3 | 0 | 2 | 3 | 0 | 5 |
| XIII | | | | | | | | | | | | |
| Lima Bean | 4 | 0 | 5,4,2 | 4 | 0 | 5,4,2 | 4 | 0 | 5,4,2 | 3 | 0 | 5,4,2 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 4 | 0 | 2 |
| Green Foxtail | 5 | 0 | 0 | 5 | 0 | 0 | 4 | 30 | 0 | 4 | 30 | 0 |
| Velvetleaf | 5 | 0 | 0 | 4 | 0 | 5 | 4 | 0 | 5 | 3 | 0 | 5 |
| Tomato | 5 | 0 | 0 | 5 | 0 | 0 | 4 | 0 | 2 | 4 | 0 | 2 |
| Bindweed | 4 | 0 | 2 | 4 | 0 | 2 | 3 | 0 | 2 | 3 | 0 | 2 |
| XIV | | | | | | | | | | | | |
| Lima Bean | 3 | 0 | 5,4,2 | 3 | 0 | 5,4,2 | 3 | 0 | 2,5 | 3 | 0 | 2,5 |
| Barnyardgrass | 5 | 0 | 0 | 5 | 0 | 0 | 5 | 0 | 0 | 5 | 0 | 0 |
| Wild Oat | 4 | 0 | 2 | 4 | 0 | 2 | 4 | 0 | 2 | 3 | 0 | 2 |
| Green Foxtail | 5 | 0 | 0 | 4 | 20 | 2 | 4 | 20 | 2 | 4 | 20 | 2 |
| Velvetleaf | 3 | 0 | 5 | 3 | 0 | 5 | 3 | 0 | 5 | 3 | 0 | 5 |
| Tomato | 4 | 0 | 2 | 4 | 0 | 2 | 3 | 0 | 2 | 3 | 0 | 5 |
| Bindweed | 4 | 0 | 2 | 4 | 0 | 2 | 3 | 0 | 2 | 3 | 30 | 2 |
| XVII | | | | | | | | | | | | |
| Lima Bean | 4 | 0 | 4,5, | 3 | 0 | 2,4,5 | 3 | 0 | 4,2,5 | 3 | 0 | 2,5 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 4 | 0 | 2 |
| Green Foxtail | 5 | 0 | 0 | 5 | 0 | 0 | 4 | 10 | 0 | 4 | 10 | 2 |
| Velvetleaf | 4 | 0 | 5 | 4 | 0 | 5 | 4 | 0 | 5 | 3 | 0 | 5 |
| Tomato | 5 | 0 | 0 | 4 | 0 | 2 | 3 | 0 | 2 | 3 | 0 | 5 |
| Bindweed | 5 | 0 | 0 | 3 | 0 | 2 | 3 | 0 | 2 | 3 | 0 | 5 |
| XVIII | | | | | | | | | | | | |
| Lima Bean | 4 | 0 | 5,4,2 | 3 | 0 | 2,5 | 3 | 0 | 4,2,5 | 3 | 0 | 2,5 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 4 | 0 | 2 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 3 | 0 | 5 | 3 | 0 | 5 |
| Tomato | 5 | 0 | 0 | 5 | 0 | 0 | 4 | 0 | 5 | 4 | 0 | 2 |
| Bindweed | 4 | 0 | 2 | 4 | 10 | 2 | 3 | 0 | 2 | 3 | 0 | 2 |
| XIX | | | | | | | | | | | | |
| Lima Bean | 4 | 0 | 2 | 4 | 0 | 4 | 4 | 0 | 2 | 4 | 0 | 5,4,2 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 5 | 0 | 0 |
| Green Foxtail | 5 | 0 | 0 | 5 | 0 | 0 | 4 | 20 | 0 | 4 | 10 | 0 |
| Velvetleaf | 5 | 0 | 0 | 5 | 0 | 0 | 4 | 0 | 2 | 4 | 0 | 5 |
| Tomato | 5 | 0 | 0 | 5 | 0 | 0 | 5 | 0 | 0 | 5 | 0 | 0 |
| Bindweed | 5 | 0 | 0 | 4 | 0 | 0 | 4 | 0 | 2 | 3 | 0 | 2 |

TABLE 6-continued

Evaluation of Preemergence Plant Regulator Activity of Substituted Benzoates

XX

| | | | | | | | | | | | | |
|---|---|---|---|---|---|---|---|---|---|---|---|---|
| Lima Bean | 4 | 0 | 5,4,2 | 4 | 0 | 5,4,2 | 3 | 0 | 5,4,2 | 3 | 0 | 4,2,5 |
| Barnyardgrass | 5 | 0 | 0 | 5 | 0 | 0 | 5 | 0 | 0 | 5 | 0 | 0 |
| Wild Oat | 5 | 0 | 0 | 4 | 0 | 2 | 4 | 0 | 2 | 4 | 0 | 2 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 4 | 0 | 2 | 4 | 0 | 5 |
| Tomato | 5 | 0 | 0 | 5 | 0 | 0 | 4 | 0 | 2 | 4 | 0 | 2 |
| Bindweed | 4 | 0 | 2 | 3 | 0 | 2 | 3 | 0 | 2 | 3 | 0 | 2 |

XXI

| | | | | | | | | | | | | |
|---|---|---|---|---|---|---|---|---|---|---|---|---|
| Lima Bean | 5 | 0 | 0 | 4 | 0 | 2 | 4 | 0 | 5,2,4 | 1 | 30 | 11 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 5 | 4 | 0 | 5 | 4 | 0 | 5 |
| Tomato | 5 | 0 | 0 | 4 | 0 | 2 | 4 | 0 | 2 | 5 | 0 | 0 |
| Bindweed | 4 | 0 | 0 | 4 | 0 | 2 | 4 | 0 | 2 | 4 | 0 | 2 |

Experiment 2*

| Compound of Example | Rate of Application (kilograms/hectare) | | | | | | | | | | | |
|---|---|---|---|---|---|---|---|---|---|---|---|---|
| | 0.50 | | | 1.00 | | | 2.00 | | | 4.00 | | |
| Plant Species | V | K | F | V | K | F | V | K | F | V | K | F |

I

| | | | | | | | | | | | | |
|---|---|---|---|---|---|---|---|---|---|---|---|---|
| Barnyardgrass | 5 | 0 | 0 | 5 | 0 | 0 | 5 | 0 | 0 | 5 | 0 | 0 |
| Wild Oat | 5 | 0 | 0 | 4 | 0 | 2 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 3 | 0 | 5 | 3 | 0 | 5 |
| Tomato | 4 | 0 | 5 | 4 | 0 | 5 | 4 | 0 | 5 | 4 | 0 | 2 |
| Bindweed | 4 | 0 | 2 | 4 | 0 | 2 | 3 | 0 | 2 | 3 | 0 | 2 |
| Lima Bean | 3 | 0 | 4 | 3 | 0 | 2 | 3 | 0 | 2 | 3 | 50 | 2 |

XVI

| | | | | | | | | | | | | |
|---|---|---|---|---|---|---|---|---|---|---|---|---|
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Tomato | 5 | 0 | 0 | 5 | 0 | 0 | 5 | 0 | 0 | 4 | 0 | 2 |
| Bindweed | 5 | 0 | 0 | 5 | 0 | 0 | 5 | 0 | 0 | 5 | 0 | 0 |
| Lima Bean | 4 | 0 | 2 | 0 | 100 | 11 | 0 | 100 | 11 | 0 | 100 | 11 |

XXII

| | | | | | | | | | | | | |
|---|---|---|---|---|---|---|---|---|---|---|---|---|
| Lima Bean | 4 | 0 | 5 | 4 | 0 | 5 | 3 | 0 | 2 | 3 | 0 | 2 |
| Barnyardgrass | 5 | 0 | 0 | 5 | 0 | 0 | 5 | 0 | 0 | 5 | 0 | 0 |
| Wild Oat | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 4 | 0 | 5 | 4 | 0 | 5 |
| Tomato | 5 | 0 | 0 | 5 | 0 | 0 | 5 | 0 | 0 | 4 | 0 | 2 |

XXIII

| | | | | | | | | | | | | |
|---|---|---|---|---|---|---|---|---|---|---|---|---|
| Lima Bean | 3 | 0 | 2 | 3 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 4 | 0 | 5 |
| Tomato | 5 | 0 | 0 | 5 | 0 | 0 | 4 | 0 | 2 | 4 | 0 | 2 |

XXIV

| | | | | | | | | | | | | |
|---|---|---|---|---|---|---|---|---|---|---|---|---|
| Lima Bean | 3 | 0 | 2 | 3 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 3 | 0 | 5 |
| Tomato | 5 | 0 | 0 | 5 | 0 | 0 | 5 | 0 | 0 | 5 | 0 | 0 |

XXV

| | | | | | | | | | | | | |
|---|---|---|---|---|---|---|---|---|---|---|---|---|
| Lima Bean | 3 | 0 | 2 | 3 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 5 | 4 | 0 | 5 | 4 | 0 | 5 |
| Tomato | 5 | 0 | 0 | 5 | 0 | 0 | 5 | 0 | 0 | 4 | 0 | 2 |

XXVI

| | | | | | | | | | | | | |
|---|---|---|---|---|---|---|---|---|---|---|---|---|
| Lima Bean | 3 | 0 | 2 | 3 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 4 | 0 | 5 |
| Tomato | 5 | 0 | 0 | 5 | 0 | 0 | 5 | 0 | 0 | 5 | 0 | 0 |

XXVII

| | | | | | | | | | | | | |
|---|---|---|---|---|---|---|---|---|---|---|---|---|
| Lima Bean | 4 | 0 | 2 | 4 | 0 | 2 | 3 | 0 | 2 | 3 | 0 | 2 |
| Barnyardgrass | 5 | 0 | 0 | 5 | 0 | 0 | 4 | 0 | 2 | 4 | 0 | 1 |
| Wild Oats | 5 | 0 | 0 | 5 | 0 | 0 | 4 | 0 | 2 | 4 | 0 | 1 |
| Green Foxtail | 5 | 0 | 0 | 5 | 0 | 0 | 4 | 0 | 2 | 4 | 0 | 2 |

TABLE 6-continued

Evaluation of Preemergence Plant Regulator Activity of Substituted Benzoates

| | | | | | | | | | | | | |
|---|---|---|---|---|---|---|---|---|---|---|---|---|
| Velvetleaf | 5 | 0 | 0 | 4 | 0 | 5 | 4 | 0 | 5 | 3 | 0 | 5 |
| Tomato | 5 | 0 | 0 | 5 | 0 | 0 | 5 | 0 | 0 | 4 | 0 | 2 |
| XXVIII | | | | | | | | | | | | |
| Barnyardgrass | 5 | 0 | 0 | 5 | 0 | 0 | 4 | 0 | 2 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 3 | 0 | 5 |
| Tomato | 5 | 0 | 0 | 4 | 0 | 2 | 4 | 0 | 2 | 3 | 0 | 5 |
| Bindweed | 4 | 0 | 2 | 4 | 0 | 2 | 4 | 0 | 2 | 4 | 0 | 5 |
| Lima Bean | 4 | 0 | 4 | 3 | 0 | 4 | 3 | 0 | 2 | 3 | 0 | 2 |
| XXIX | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 5 | 4 | 0 | 5 | 4 | 0 | 5 |
| Tomato | 5 | 0 | 0 | 4 | 0 | 5 | 5 | 0 | 0 | 4 | 0 | 2 |
| Bindweed | 5 | 0 | 0 | 4 | 0 | 2 | 4 | 0 | 2 | 4 | 0 | 2 |
| Lima Bean | 4 | 0 | 4 | 3 | 0 | 4 | 3 | 0 | 2 | 3 | 0 | 2 |
| XXX | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 4 | 0 | 5 |
| Tomato | 5 | 0 | 0 | 4 | 0 | 5 | 4 | 0 | 2 | 4 | 0 | 5 |
| Bindweed | 5 | 0 | 0 | 5 | 0 | 0 | 4 | 0 | 2 | 4 | 0 | 2 |
| Lima Bean | 3 | 0 | 4 | 4 | 0 | 4 | 3 | 0 | 2 | 3 | 0 | 2 |

*See Table 1 for definition of Vigor (V) and Footnote (F) code designations; K refers to percent kill.

TABLE 7

Evaluation of Postemergence Plant Regulator Activity of Substituted Benzoates

Experiment 1*

| Compound of Example | Rate of Application (kilograms/hectare) | | | | | | | | | | | |
|---|---|---|---|---|---|---|---|---|---|---|---|---|
| | 0.56 | | | 1.12 | | | 2.24 | | | 4.48 | | |
| Plant Species | V | K | F | V | K | F | V | K | F | V | K | F |
| I | | | | | | | | | | | | |
| Lima Bean | 3 | 0 | 2 | 3 | 0 | 2 | 3 | 0 | 2 | 3 | 0 | 2,1 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 5 | 4 | 0 | 5 | 4 | 0 | 5 |
| Tomato | 4 | 0 | 2 | 4 | 0 | 2 | 4 | 0 | 2 | 4 | 0 | 5 |
| Bindweed | 4 | 0 | 5 | 4 | 0 | 5 | 4 | 0 | 5 | 3 | 0 | 5 |
| XIII | | | | | | | | | | | | |
| Lima Bean | 4 | 0 | 4,2,5 | 3 | 0 | 4,2,5 | 3 | 0 | 4,2,5 | 3 | 0 | 4,2,5,10 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 0 | 100 | 12 | 5 | 0 | 0 |
| Velvetleaf | 5 | 0 | 0 | 4 | 0 | 5 | 4 | 0 | 5 | 3 | 0 | 5 |
| Tomato | 4 | 0 | 5 | 4 | 0 | 5 | 4 | 0 | 5 | 3 | 0 | 2 |
| Bindweed | 5 | 0 | 0 | 5 | 0 | 0 | 4 | 0 | 5 | 4 | 0 | 5 |
| XIV | | | | | | | | | | | | |
| Lima Bean | 3 | 0 | 4,2,5 | 3 | 0 | 2,5 | 3 | 0 | 2 | 3 | 0 | 2,5,10 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 4 | 0 | 2 |
| Green Foxtail | 5 | 0 | 0 | 5 | 0 | 0 | 5 | 0 | 0 | 5 | 0 | 0 |
| Velvetleaf | 3 | 0 | 2 | 3 | 0 | 2 | 3 | 0 | 5 | 3 | 0 | 2 |
| Tomato | 3 | 0 | 2 | 3 | 0 | 2 | 3 | 0 | 2 | 3 | 0 | 2 |
| Bindweed | 4 | 0 | 5 | 4 | 0 | 5 | 4 | 0 | 2 | 4 | 0 | 2 |
| XVII | | | | | | | | | | | | |
| Lima Bean | 3 | 0 | 4,2,5 | 3 | 0 | 4,2,5 | 3 | 0 | 2,4 | 3 | 0 | 2,4 |
| Barnyardgrass | 5 | 0 | 0 | 4 | 0 | 2 | 4 | 0 | 2 | 4 | 0 | 2 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 2 | 4 | 0 | 5 | 4 | 0 | 5 |
| Tomato | 5 | 0 | 0 | 4 | 0 | 2 | 4 | 0 | 5 | 4 | 0 | 5 |
| Bindweed | 5 | 0 | 0 | 5 | 0 | 0 | 4 | 0 | 5 | 4 | 0 | 5 |
| XVIII | | | | | | | | | | | | |
| Lima Bean | 3 | 0 | 4,2,5 | 3 | 0 | 4,2,5 | 3 | 0 | 2,4,5 | 3 | 0 | 2,4,5 |
| Barnyardgrass | 4 | 0 | 2 | 5 | 0 | 0 | 4 | 0 | 2 | 4 | 0 | 2 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 0 | 100 | 12 |
| Velvetleaf | 4 | 0 | 2 | 4 | 0 | 5 | 4 | 0 | 5 | 3 | 0 | 5 |
| Tomato | 5 | 0 | 0 | 4 | 0 | 5 | 4 | 0 | 5 | 4 | 0 | 5 |

TABLE 7-continued

Evaluation of Postemergence Plant Regulator Activity of Substituted Benzoates

| | | | | | | | | | | | | |
|---|---|---|---|---|---|---|---|---|---|---|---|---|
| Bindweed | 5 | 0 | 0 | 4 | 0 | 5 | 4 | 0 | 2 | 4 | 0 | 5 |
| XIX | | | | | | | | | | | | |
| Lima Bean | 4 | 0 | 2,4 | 4 | 0 | 4,5 | 3 | 0 | 2,4,5 | 4 | 0 | 5,4 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 4 | 0 | 2 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 4 | 0 | 5 |
| Tomato | 4 | 0 | 5 | 4 | 0 | 5 | 4 | 0 | 5 | 4 | 0 | 5 |
| Bindweed | 5 | 0 | 0 | 4 | 0 | 5 | 4 | 0 | 5 | 4 | 0 | 5 |
| XX | | | | | | | | | | | | |
| Lima Bean | 4 | 0 | 4,2,5 | 4 | 0 | 2,4,5 | 4 | 0 | 4,2,5 | 3 | 0 | 4,2,5 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 4 | 0 | 5 |
| Tomato | 4 | 0 | 5 | 4 | 0 | 5 | 4 | 0 | 5 | 4 | 0 | 5 |
| Bindweed | 4 | 0 | 5 | 4 | 0 | 5 | 4 | 0 | 2 | 4 | 0 | 2 |
| XXI | | | | | | | | | | | | |
| Lima Bean | 4 | 0 | 4,2,5 | 4 | 0 | 4,2,5 | 4 | 0 | 4,2,5 | 3 | 0 | 2,5 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 4 | 0 | 5 | 4 | 0 | 5 |
| Tomato | 4 | 0 | 5 | 4 | 0 | 5 | 4 | 0 | 5 | 4 | 0 | 5 |
| Bindweed | 5 | 0 | 0 | 5 | 0 | 0 | 5 | 0 | 0 | 4 | 0 | 5 |

Experiment 2*

| Compound of Example | Rate of Application (kilograms/hectare) | | | | | | | | | | | |
|---|---|---|---|---|---|---|---|---|---|---|---|---|
| | 0.50 | | | 1.00 | | | 2.00 | | | 4.00 | | |
| Plant Species | V | K | F | V | K | F | V | K | F | V | K | F |
| I | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 3 | 0 | 5 | 3 | 0 | 5 |
| Tomato | 4 | 0 | 2 | 4 | 0 | 5 | 4 | 0 | 5 | 4 | 0 | 5 |
| Bindweed | 4 | 0 | 2 | 4 | 0 | 2 | 4 | 0 | 2 | 3 | 0 | 2 |
| Lima Bean | 3 | 0 | 2 | 3 | 0 | 2 | 3 | 0 | 2 | 3 | 0 | 2 |
| XVI | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 4 | 0 | 5 |
| Tomato | 5 | 0 | 0 | 5 | 0 | 0 | 5 | 0 | 0 | 5 | 0 | 0 |
| Bindweed | 5 | 0 | 0 | 5 | 0 | 0 | 5 | 0 | 0 | 5 | 0 | 0 |
| Lima Bean | 5 | 0 | 0 | 4 | 0 | 6 | 4 | 0 | 9 | 4 | 0 | 6 |
| XXII | | | | | | | | | | | | |
| Lima Bean | 4 | 0 | 2 | 4 | 0 | 2 | 4 | 0 | 2 | 4 | 0 | 2 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 5 | 0 | 0 | 5 | 0 | 0 |
| Tomato | 5 | 0 | 0 | 4 | 0 | 1 | 4 | 20 | 1 | 3 | 10 | 1 |
| XXIII | | | | | | | | | | | | |
| Lima Bean | 3 | 0 | 2 | 3 | 0 | 2 | 3 | 0 | 2 | 2 | 0 | 1 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 5 | 4 | 0 | 5 | 4 | 0 | 5 |
| Tomato | 3 | 30 | 12 | 4 | 0 | 1 | 4 | 0 | 2 | 3 | 0 | 2 |
| XXIV | | | | | | | | | | | | |
| Lima Bean | 3 | 0 | 2 | 3 | 0 | 2 | 2 | 0 | 2 | 2 | 60 | 1 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 4 | 0 | 5 |
| Tomato | 4 | 0 | 2 | 4 | 0 | 2 | 4 | 0 | 2 | 3 | 0 | 2 |
| XXV | | | | | | | | | | | | |
| Lima Bean | 4 | 0 | 5 | 4 | 0 | 2 | 3 | 0 | 2 | 4 | 0 | 2 |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 5 | 0 | 0 | 4 | 0 | 5 | 4 | 0 | 5 |
| Tomato | 5 | 0 | 0 | 4 | 20 | 1 | 4 | 20 | 1 | 3 | 20 | 1 |
| XXVI | | | | | | | | | | | | |
| Lima Bean | 3 | 0 | 2 | 3 | 0 | 2 | 3 | 0 | 2 | 3 | 0 | 2 |
| Barnyardgrass | 5 | 0 | 0 | 5 | 0 | 0 | 5 | 0 | 0 | 5 | 0 | 0 |

TABLE 7-continued
Evaluation of Postemergence Plant Regulator Activity of Substituted Benzoates

| | | | | | | | | | | | | |
|---|---|---|---|---|---|---|---|---|---|---|---|---|
| Wild Oats | 5 | 0 | 0 | 4 | 0 | 2 | 4 | 0 | 2 | 5 | 0 | 0 |
| Green Foxtail | 5 | 0 | 0 | 5 | 0 | 0 | 5 | 0 | 0 | 5 | 0 | 0 |
| Velvetleaf | 5 | 0 | 0 | 4 | 0 | 5 | 4 | 0 | 5 | 4 | 0 | 5 |
| Tomato | 4 | 0 | 1 | 3 | 0 | 2 | 4 | 20 | 1 | 3 | 0 | 2 |
| XXVII | | | | | | | | | | | | |
| Lima Bean | 4 | 0 | 5 | 4 | 0 | 5 | 4 | 0 | 1 | 3 | 0 | 2 |
| Barnyardgrass | 5 | 0 | 0 | 5 | 0 | 0 | 5 | 0 | 0 | 4 | 0 | 1 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 3 | 0 | 5 | 3 | 0 | 2 |
| Tomato | 5 | 0 | 0 | 5 | 0 | 0 | 4 | 0 | 1 | 3 | 0 | 1 |
| XXVIII | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 3 | 0 | 5 | 3 | 0 | 5 |
| Tomato | 4 | 0 | 2 | 4 | 0 | 2 | 3 | 0 | 2 | 2 | 0 | 2 |
| Bindweed | 4 | 0 | 2 | 4 | 0 | 2 | 4 | 0 | 2 | 4 | 0 | 2 |
| Lima Bean | 3 | 0 | 2 | 3 | 0 | 2 | 3 | 0 | 2 | 3 | 0 | 2 |
| XXIX | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 4 | 90 | 12 |
| Velvetleaf | 4 | 0 | 5 | 4 | 0 | 5 | 4 | 0 | 5 | 3 | 0 | 5 |
| Tomato | 5 | 0 | 0 | 5 | 0 | 0 | 4 | 0 | 2 | 3 | 0 | 2 |
| Bindweed | 4 | 0 | 2 | 4 | 0 | 2 | 3 | 0 | 2 | 4 | 0 | 2 |
| Lima Bean | 3 | 0 | 4 | 3 | 0 | 2 | 3 | 0 | 2 | 2 | 0 | 10 |
| XXX | | | | | | | | | | | | |
| Barnyardgrass | 5 | 0 | 0 | 5 | 0 | 0 | 5 | 0 | 0 | 5 | 0 | 0 |
| Wild Oats | 5 | 0 | 0 | 5 | 0 | 0 | 5 | 0 | 0 | 5 | 0 | 0 |
| Green Foxtail | 5 | 0 | 0 | 5 | 0 | 0 | 5 | 0 | 0 | 5 | 0 | 0 |
| Velvetleaf | 4 | 0 | 5 | 4 | 0 | 5 | 4 | 0 | 5 | 3 | 0 | 5 |
| Tomato | 4 | 0 | 2 | 4 | 0 | 2 | 3 | 0 | 2 | 3 | 0 | 2 |
| Bindweed | 5 | 0 | 0 | 5 | 0 | 0 | 4 | 0 | 2 | 4 | 0 | 2 |
| Lima Bean | 3 | 0 | 4 | 3 | 0 | 4 | 3 | 0 | 2 | 3 | 0 | 2 |

*See Table 1 for definition of Vigor (V) and Footnote (F) code designations; K refers to percent kill.

TABLE 8
Effect of Plant Regulator Compounds on Lima Bean Flowering (F) and Vigor*

| Compound of | Rate of Application (kilograms/hectare) | | | | | | |
|---|---|---|---|---|---|---|---|
| Example | 0.07 | 0.14 | 0.28 | 0.56 | 1.12 | 2.24 | 4.48 |
| I | 3 | 3F | 3 | 3 | 3 | 3 | 3 |
| XIII | 4F | 4F | 4F | 4F | 3 | 3 | 3 |
| XIV | 4F | 4 | 4 | 3 | 3 | 3 | 2 |
| XVII | 4F | 4F | 4 | 3 | 3 | 3 | 3 |
| XVIII | 4 | 4F | 4F | 3F | 3 | 3 | 3 |
| XIX | 4F | 4 | 4F | 4F | 4F | 3F | 3 |
| XX | 4 | 4 | 4F | 4 | 4 | 4 | 3 |
| XXI | 4F | 4 | 4 | 4F | 4F | 4F | 3 |
| Untreated | — | — | 5 | — | — | — | — |

*Vigor:
5 = Plants normal.
4 = Slight injury; plants will or have already recovered.
3 = Moderate injury; plants expected to recover.

TABLE 9
Effect of Plant Regulator Compounds on Lima Bean Pod Formation*

| Compound of | Rate of Application (kilograms/hectare) | | | | | | |
|---|---|---|---|---|---|---|---|
| Example | 0.07 | 0.14 | 0.28 | 0.56 | 1.12 | 2.24 | 4.48 |
| I | 0 | 0 | 0 | 0 | 0 | 0 | 0 |
| XIII | 1P | 3P | 3P | 0 | 0 | 0 | 0 |
| XIV | 1P | 0 | 0 | 0 | 0 | 0 | 0 |
| XVII | 1P | 2P | 0 | 0 | 0 | 0 | 0 |
| XVIII | 2P | 1P | 1P | 0 | 0 | 0 | 0 |
| XIX | 1P | 1P | 2P | 2P | 2P | 0 | 0 |
| XX | 1P | 1P | 2P | 0 | 0 | 0 | 0 |
| XXI | 0 | 1P | 0 | 2P | 0 | 0 | 0 |
| Untreated | — | — | 1P/4 Plants | — | — | — | — |

*No. pods one inch or more in length on single test plant.

We claim:

1. A compound of the formula $$X_n-\underset{}{\bigcirc}-\overset{O}{\underset{\|}{C}}-O-R'-Y$$

wherein
R' is straight or branched alkylene of 1 to 4 carbons;
Y is $$-\overset{O}{\underset{\|}{C}}-Z;$$

Z is —NH$_2$, —NHR, —NR$_1$R$_2$, —NH—NR$_1$R$_2$;
R$_1$ and R$_2$ are the same or different and are alkyl of 1 to 4 carbons or phenyl;
X is chlorine, occurring in the 2- and 6-positions in the benzene ring;
n is 2.

2. The compound of claim 1 in which R' is alkylene of 1 to 3 carbons; and R$_1$ and R$_2$ are methyl or ethyl.

3. The compound of claim 2 in which R' is methylene; and Z is —NH$_2$ or —NR$_1$R$_2$.

4. The compound of claim 3 which is (aminocarbonyl)methyl 2,6-dichlorobenzoate.

* * * * *